United States Patent
Keränen et al.

(10) Patent No.: US 10,517,724 B2
(45) Date of Patent: Dec. 31, 2019

(54) MEDICAL SYSTEM FOR ANNULOPLASTY

(71) Applicant: Medtentia International Ltd Oy, Helsinki (FI)

(72) Inventors: Olli Keränen, Bjärred (SE); Hans-Reinhard Zerkowski, Kreuzlingen (CH)

(73) Assignee: Medtentia International Ltd. Oy, Helsinki (FI)

( * ) Notice: Subject to any disclaimer, the term of this patent is extended or adjusted under 35 U.S.C. 154(b) by 0 days.

(21) Appl. No.: 14/891,939

(22) PCT Filed: May 21, 2014

(86) PCT No.: PCT/EP2014/060434
§ 371 (c)(1),
(2) Date: Nov. 17, 2015

(87) PCT Pub. No.: WO2014/187855
PCT Pub. Date: Nov. 27, 2014

(65) Prior Publication Data
US 2016/0095705 A1    Apr. 7, 2016

(30) Foreign Application Priority Data
May 21, 2013 (EP) .................................. 13168600

(51) Int. Cl.
*A61F 2/24* (2006.01)
*A61B 17/12* (2006.01)
(Continued)

(52) U.S. Cl.
CPC ...... *A61F 2/2445* (2013.01); *A61B 17/00234* (2013.01); *A61B 17/068* (2013.01);
(Continued)

(58) Field of Classification Search
CPC .... A61F 2/2451; A61F 2/2466; A61F 2/2442; A61F 2/2445
See application file for complete search history.

(56) References Cited

U.S. PATENT DOCUMENTS 7,144,363 B2* 12/2006 Pai ................... A61B 17/00234
600/16
2002/0055772 A1* 5/2002 McGuckin, Jr. .......... A61F 2/82
623/1.24
(Continued)

FOREIGN PATENT DOCUMENTS

| EP | 2072027 A1 | 6/2009 |
|---|---|---|
| WO | WO2002/062270 A1 | 8/2002 |
| WO | WO2004/084746 A2 | 10/2004 |

OTHER PUBLICATIONS

WIPO, International Preliminary Examining Authority (European Patent Office), International Preliminary Report on Patentability dated Sep. 7, 2015 in International Patent Application No. PCT/EP2014/060434, 104 pages.
(Continued)

*Primary Examiner* — Dinah Baria
(74) *Attorney, Agent, or Firm* — Inskeep IP Group, Inc.

(57) ABSTRACT

A medical system for treating a defective mitral valve (MV) having an annulus (A). The system has a removable and flexible elongate displacement unit for temporary insertion into a coronary sinus (CS) adjacent the valve, wherein the displacement unit has a delivery state for delivery into said CS, and an activated state to which the displacement unit is temporarily and reversibly transferable from the delivery state. The displacement unit has a proximal reversibly expandable portion, a distal anchoring portion being movable in relation to the proximal expandable portion in a longitudinal direction of the displacement unit to the activated state in which the shape of the annulus is modified to
(Continued)

a modified shape (A'); and an annuloplasty device for permanent fixation at the mitral valve annulus by annuloplasty of the valve when the modified shape is obtained.

19 Claims, 18 Drawing Sheets

(51) Int. Cl.
    *A61B 17/00*     (2006.01)
    *A61B 17/068*     (2006.01)
    *A61B 17/072*     (2006.01)
    *A61B 17/02*     (2006.01)
    *A61B 17/064*     (2006.01)

(52) U.S. Cl.
    CPC ........ *A61B 17/072* (2013.01); *A61B 17/1204* (2013.01); *A61B 17/12036* (2013.01); *A61B 17/12109* (2013.01); *A61B 17/12136* (2013.01); *A61B 17/12163* (2013.01); *A61F 2/2442* (2013.01); *A61F 2/2451* (2013.01); *A61F 2/2466* (2013.01); *A61B 17/0218* (2013.01); *A61B 17/0644* (2013.01); *A61F 2230/0091* (2013.01); *A61F 2250/0003* (2013.01); *A61F 2250/0059* (2013.01)

(56) References Cited

U.S. PATENT DOCUMENTS

| | | |
|---|---|---|
| 2004/0153147 A1 | 8/2004 | Mathis |
| 2005/0197694 A1 | 9/2005 | Pai et al. |
| 2007/0185572 A1 | 8/2007 | Solem et al. |
| 2008/0103590 A1 | 5/2008 | Taylor et al. |
| 2010/0331971 A1* | 12/2010 | Keranen ............... A61F 2/2445 623/2.11 |
| 2017/0065416 A1* | 3/2017 | Zerkowski ............ A61F 2/2451 |

OTHER PUBLICATIONS

WIPO, European International Search Authority, International Search Report dated Oct. 21, 2014 in International Patent Application No. PCT/EP2014/060434, 7 pages.

* cited by examiner

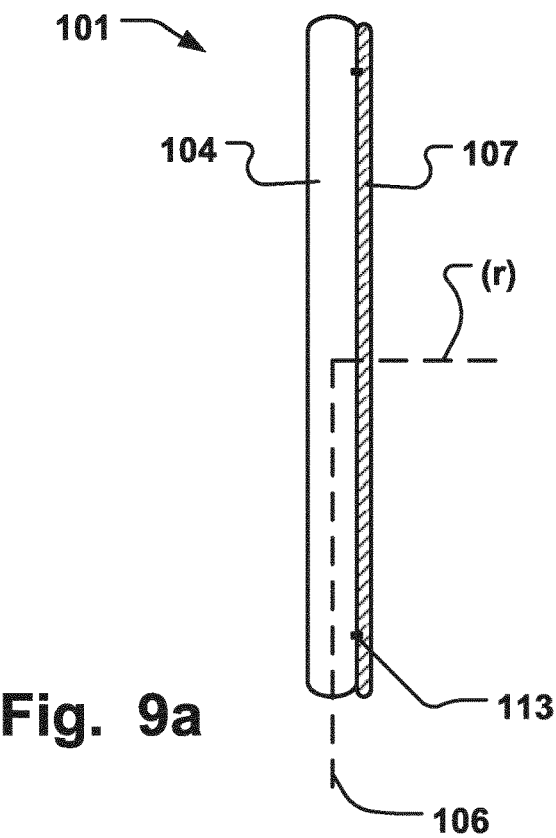
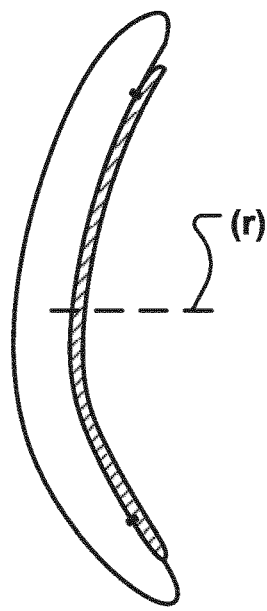
Fig. 9a  Fig. 9b
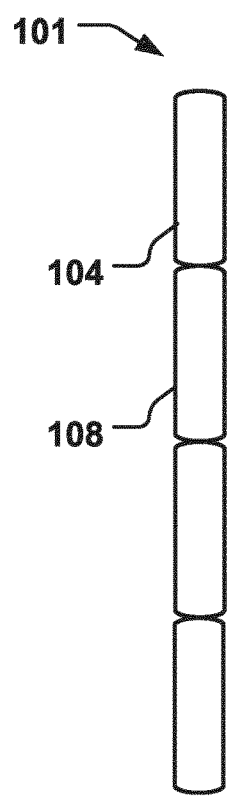
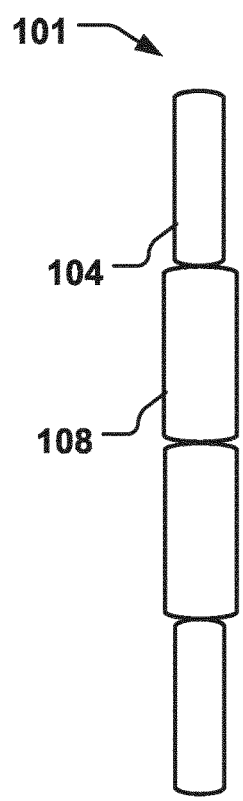
Fig. 10a  Fig. 10b

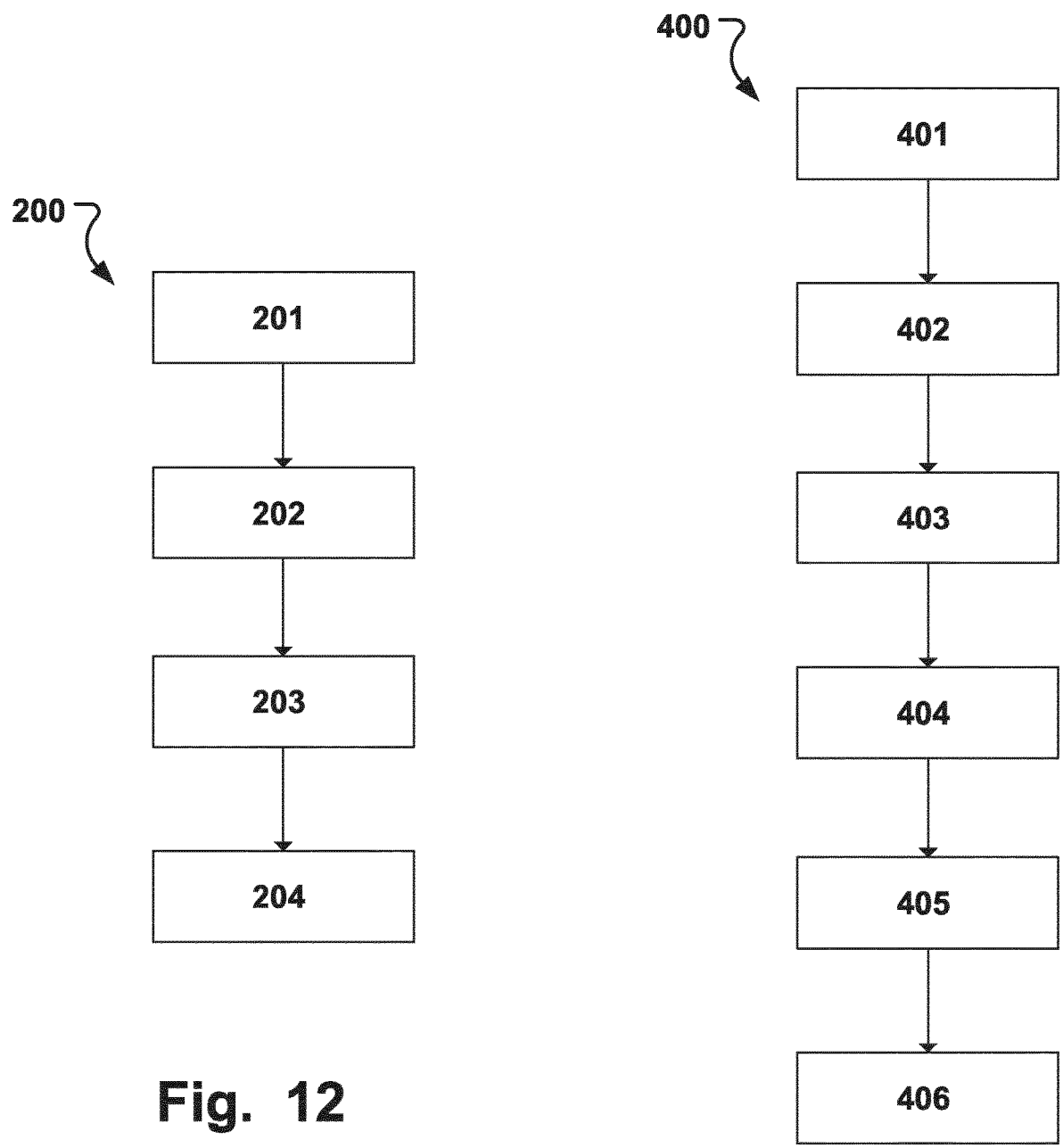

MEDICAL SYSTEM FOR ANNULOPLASTY

RELATED APPLICATIONS

This application is the U.S. National Phase of and claims priority to International Patent Application No. PCT/EP2014/060434, International Filing Date May 21, 2014, entitled Medical System For Annuloplasty, which claims benefit of European Patent Application No. EP13168600.8, filed May 21, 2013 entitled Medical System For Annuloplasty, both of which are incorporated herein by reference in their entireties.

FIELD OF THE INVENTION

This invention pertains in general to the field of annuloplasty devices for treating a defective mitral valve. More particularly the invention relates to a medical system of devices for treating a defective mitral valve via coronary sinus and an annuloplasty implant for fixation of the annulus, and a method therefore.

BACKGROUND OF THE INVENTION

Diseased mitral valves frequently need repair to function properly. The mitral valve leaflets or supporting chordae may degenerate and weaken or the annulus may dilate leading to valve leak (valve insufficiency). Mitral valve repair is frequently performed with aid of an annuloplasty ring, used to reduce the diameter of the annulus, or modify the geometry of the annulus in any other way, or aid as a generally supporting structure during the valve replacement or repair procedure.

Implants have previously been introduced into the coronary sinus (CS) in order to affect the shape of the valve annulus and thereby the valve function. U.S. Pat. No. 6,210,432 and WO02/062270 discloses such implant that is aimed to replace annuloplasty rings. Permanent implant have several disadvantageous effects, for example since they are implanted into the CS which is a source for later complications.

Thus, a problem with the prior art implants in the CS is that such implants may be less effective in retaining the desired geometry of the annulus. It may be necessary for the implants to be positioned in the CS for a lengthy time in order to sustain the correct function of the valve. This pose significant requirements on the long-term function of the implant, that may not implants as effective as annuloplasty rings to start with. A further problem with prior art is thus that complex and difficult-to-operate devices must be deployed in the CS, that may require frequent adjustment and repositioning to ensure the correct function over time. Another problem with prior art devices is the traumatic effects on the CS itself, due to fixation structures that must ensure the correct position of the device in the CS over time. Another problem is to ensure that a significant part of the annulus is reshaped while providing for atraumatic engagement with the anatomy.

EP2072027 discloses a device for insertion into the CS. It is a segmented device that can change its radius. A balloon at the distal end for providing a temporary fixation point at the distal end is disclosed.

The above problems may have dire consequences for the patient and the health care system. Patient risk is increased.

Hence, an improved medical system for performing downsizing and reshaping of the valve annulus would be advantageous and in particular allowing for ensuring long-term functioning, less complex procedure, and less traumatic effects on the anatomy and increased patient safety.

Also, a method of downsizing and reshaping the mitral valve annulus with such medical system would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a medical system for treating a defective mitral valve (MV) having an annulus (A) is provided. The system comprises in combination a removable and flexible elongate displacement unit for temporary insertion into a coronary sinus (CS) adjacent the valve, wherein the displacement unit has a delivery state for delivery into said CS, and an activated state to which the displacement unit is temporarily and reversibly transferable from the delivery state. The displacement unit comprises a proximal reversibly expandable portion, a distal anchoring portion being movable in relation to the proximal expandable portion in a longitudinal direction of the displacement unit to the activated state in which the shape of the annulus is modified to a modified shape (A'); and an annuloplasty device for permanent fixation at the mitral valve annulus by annuloplasty of the valve when the modified shape is obtained. The annuloplasty device comprises a fixation structure that is adapted to retain the modified shape.

According to a second aspect of the invention a method is provided for treating a defective mitral valve having an annulus, where the method comprises; inserting a flexible and removable elongate displacement unit in a delivery state into a coronary sinus (CS) adjacent said valve, positioning a proximal expandable portion against a tissue wall at the entrance of said CS, positioning a distal anchoring portion inside said CS, activating said displacement unit in an activated state whereby said distal anchoring portion is moved in a longitudinal direction of said displacement unit to reduce the distance (L) between said distal anchoring portion and said proximal expandable portion, to a shorter or reduced distance (L') such that the shape of the annulus is modified to a modified shape (A'), fixating an annuloplasty device at the mitral valve annulus when said modified shape is obtained, whereby said annuloplasty device comprises a fixation structure that is adapted to retain said modified shape, removing said elongate displacement unit after temporary activation in the activated state.

According to a third aspect of the invention a removable and flexible elongate displacement unit for temporary insertion into a coronary sinus (CS) adjacent a defective mitral valve (MV) having an annulus (A) is disclosed. The displacement unit has a delivery state for delivery into said CS, and an activated state to which the displacement unit is temporarily and reversibly transferable from said delivery state. The displacement unit comprises a proximal reversibly expandable portion, a distal anchoring portion being movable in relation to said proximal expandable portion in a longitudinal direction of said displacement unit to said activated state in which the shape of the annulus is modified to a modified shape (A').

According to a fourth aspect of the invention a medical system for treating a defective mitral valve having an annulus is provided, where the medical system comprises in combination; a removable elongate displacement unit for temporary insertion into a coronary sinus (CS) adjacent the mitral valve, wherein the displacement unit has a delivery state for delivery into the CS, and an activated state to which the displacement unit is temporarily and reversibly transferable from the delivery state, whereby at least a portion of the displacement unit is temporarily movable in a radial direction of the CS towards the valve in such a manner that the shape of the annulus is modified to a modified shape. The medical system further comprising an annuloplasty device for permanent fixation at the mitral valve annulus by annuloplasty of the valve when the modified shape is obtained, wherein the annuloplasty device comprises a fixation structure that is adapted to retain the modified shape.

According to a fifth aspect of the invention a method is provided for treating a defective mitral valve having an annulus, where the method comprises; inserting a removable elongate displacement unit in a delivery state into a coronary sinus (CS) adjacent the mitral valve;

activating the displacement unit in an activated state whereby at least a portion of the displacement unit is moved in a radial direction of the CS towards the valve in such a manner that the shape of the annulus is modified to a modified shape; fixating an annuloplasty device at the mitral valve annulus when then modified shape is obtained, whereby the annuloplasty device comprises a fixation structure that is adapted to retain the modified shape; and removing the elongate displacement unit after temporary activation in the activated state.

Further embodiments of the invention are defined in the dependent claims, wherein features for the second and subsequent aspects of the invention are as for the first aspect mutatis mutandis. In particular, features of the first aspect of the invention as defined in the dependent claims to the first aspect of the invention are also applied to the third aspect of the invention.

Some embodiments of the invention provide for long-term functioning of the mitral valve.

Some embodiments of the invention provide for less complex downsizing procedures of the mitral valve.

Some embodiments of the invention provide for a reduced risk of damaging the anatomy such as the CS.

Some embodiments of the invention provide for a secure downsizing while at the same time reducing the risk of damaging the anatomy such as the CS.

Some embodiments of the invention provide for improved downsizing of the mitral valve annulus while ensuring an atraumatic procedure.

Some embodiments of the invention also provide for reduced risk of long-term negative effects of CS implants.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 9a-b are illustrations of a part of a medical system according to embodiments of the invention in a top-down view;

FIGS. 10a-b are illustrations of a part of a medical system according to embodiments of the invention in a top-down view;

FIG. 12 is a flow chart illustrating a method of treating a defective mitral valve according to embodiments of the invention;

FIG. 20 is a flow chart illustrating a method of treating a defective mitral valve according to embodiments of the invention.

DESCRIPTION OF EMBODIMENTS

Figure 1:
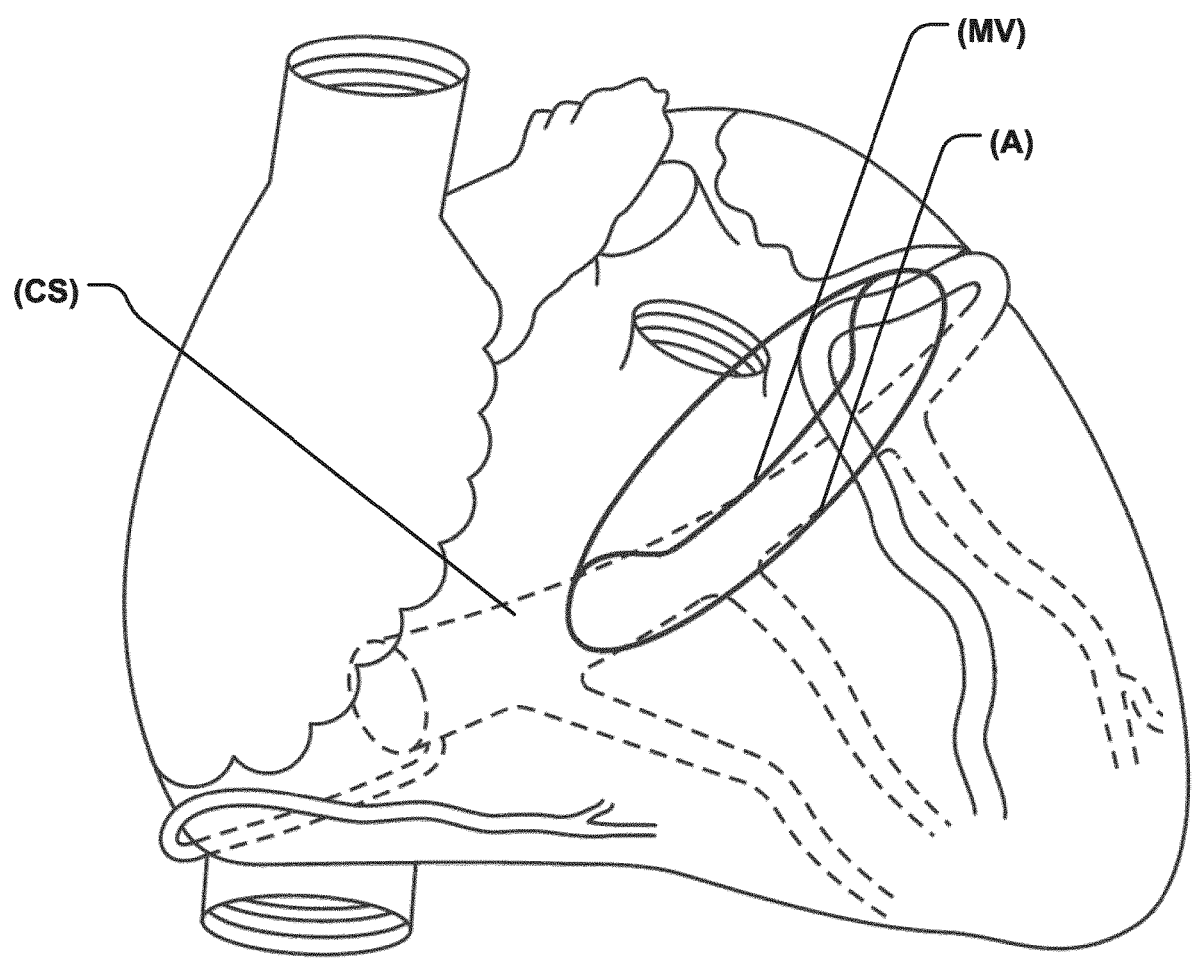
FIG. 1 is an illustration of the heart showing the coronary sinus in relation to the mitral valve in a side-view.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to treatment of defective mitral valves by repairing of the native valve. However, it will be appreciated that the invention is not limited to this application but may be applied to many other annuloplasty procedures including for example replacement valves, and other medical implantable devices.

Figure 2A:
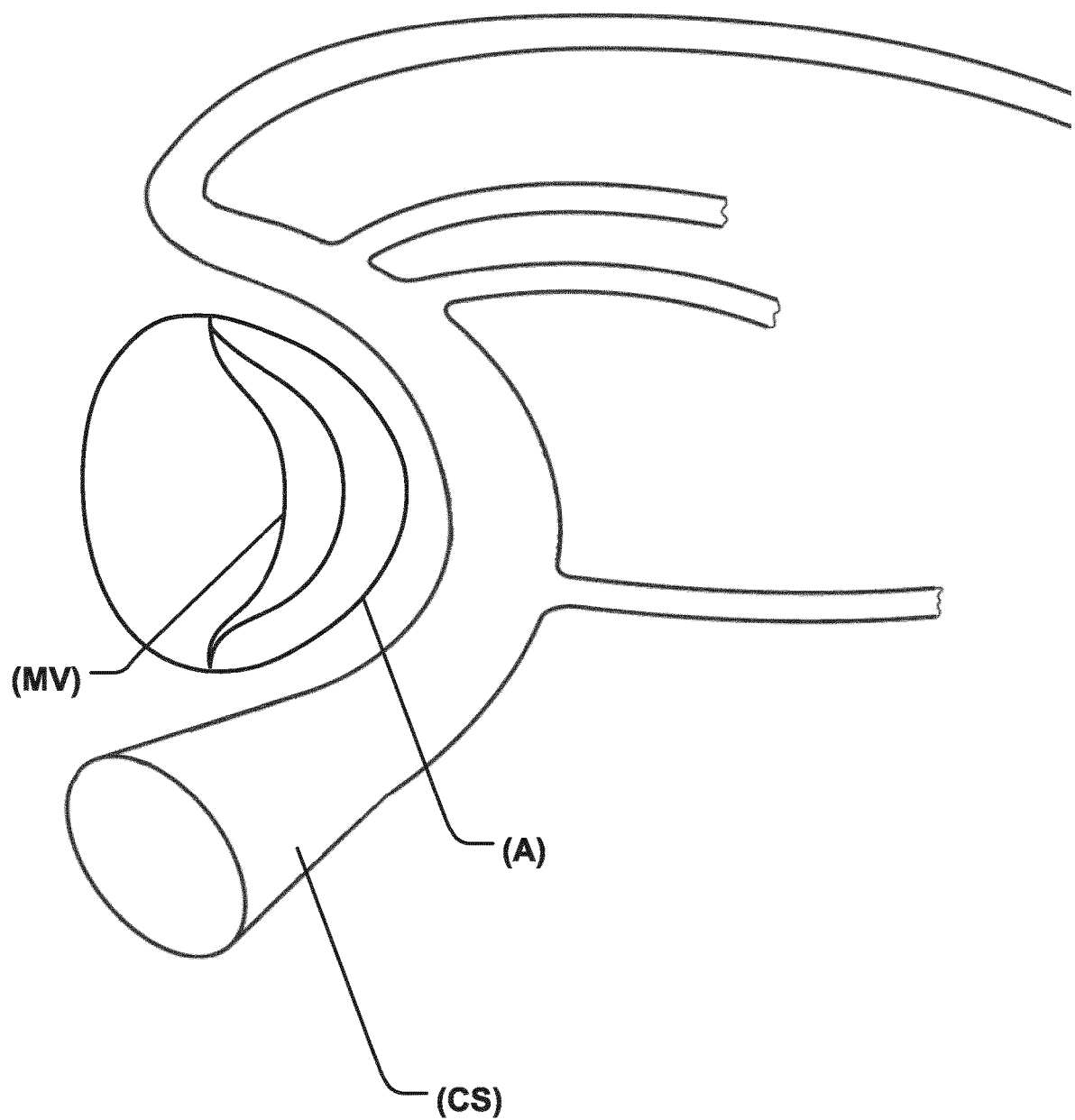
FIG. 2a is an illustration of the heart showing the coronary sinus in relation to a diseased mitral valve in a top-down view.

FIG. 1 is an illustration of the heart showing the coronary sinus (CS) in relation to the mitral valve (MV) in a side-view. The CS lies adjacent the MV and follows a curvature around the annulus (A) of the MV, which is further illustrated in the top-down view of FIG. 2a.

Figure 2B:
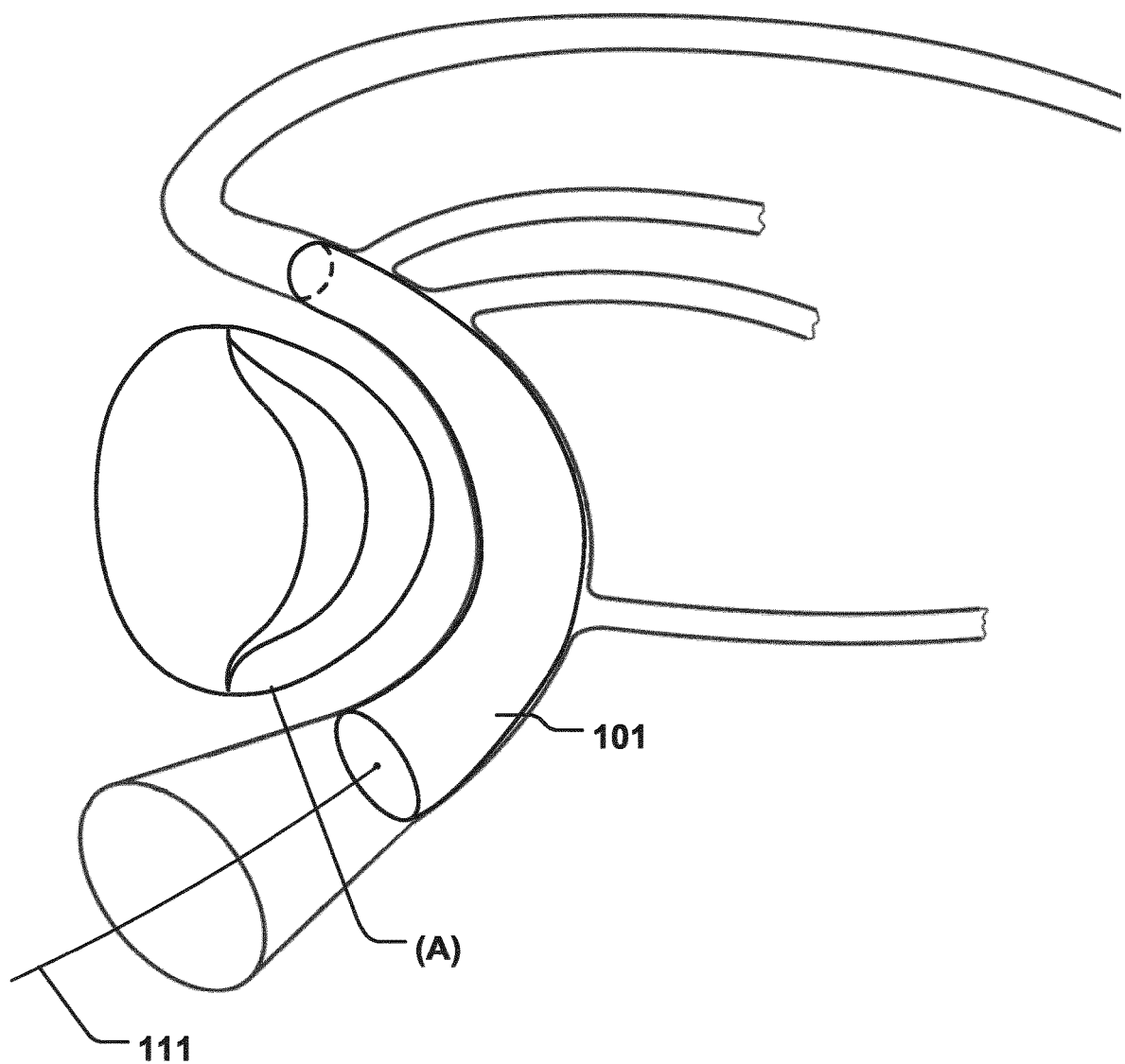
FIG. 2b is an illustration of a part of a medical system according to embodiments of the invention in a first state.
Figure 2C:
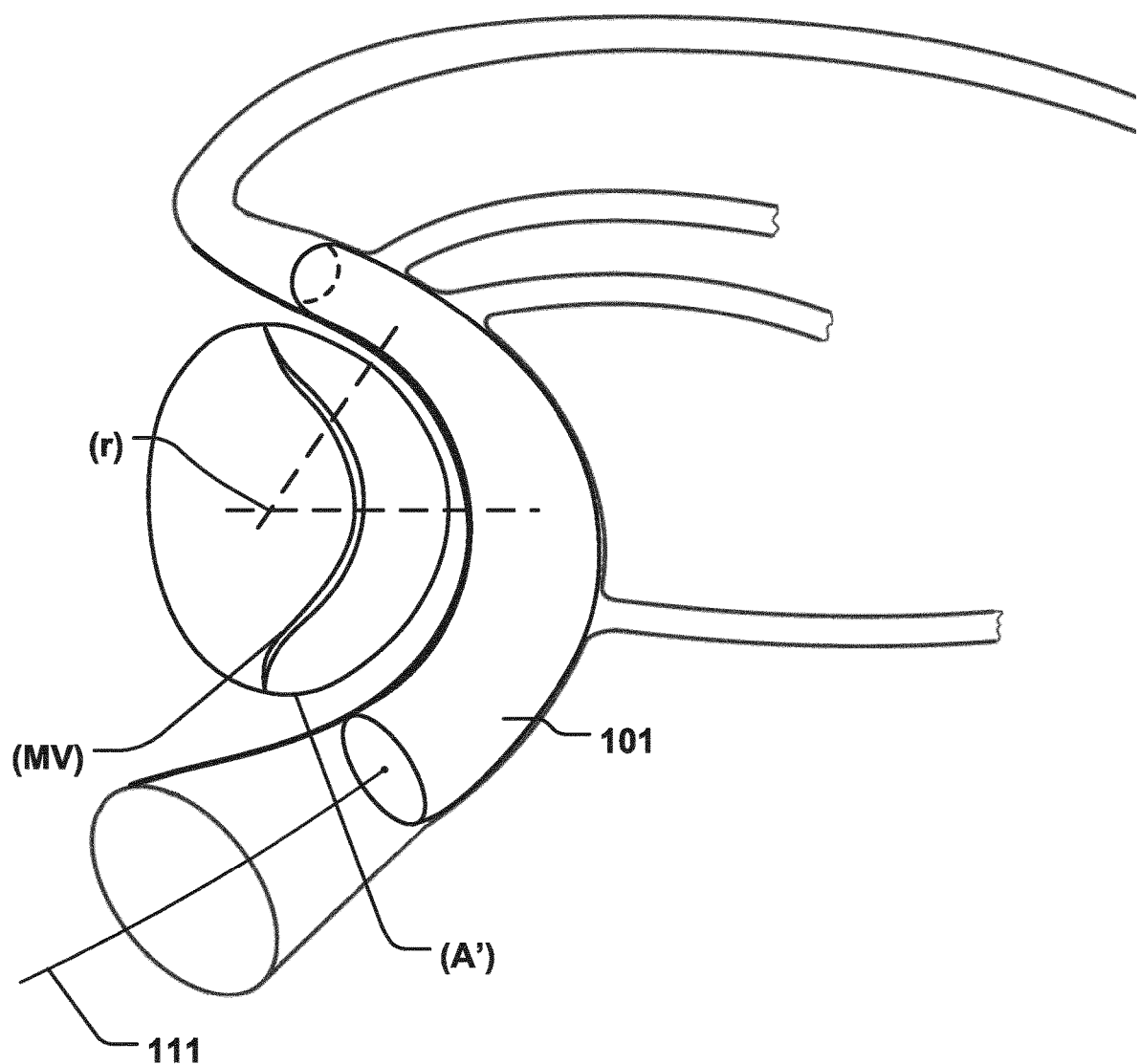
FIG. 2c is an illustration of a part of a medical system according to embodiments of the invention in a second state.
Figure 2D:
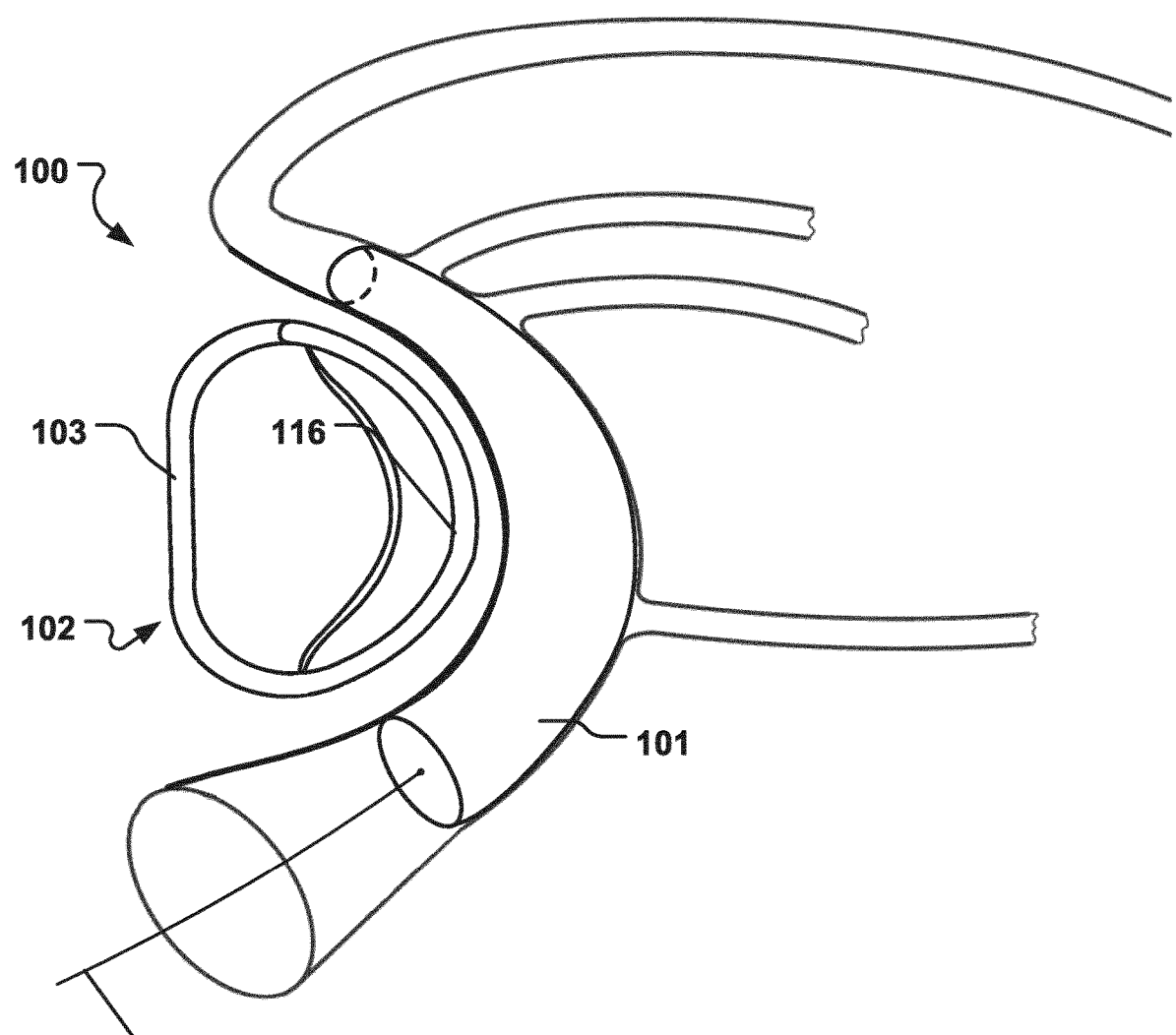
FIG. 2d is an illustration of a medical system according to embodiments of the invention.
Figure 2E:
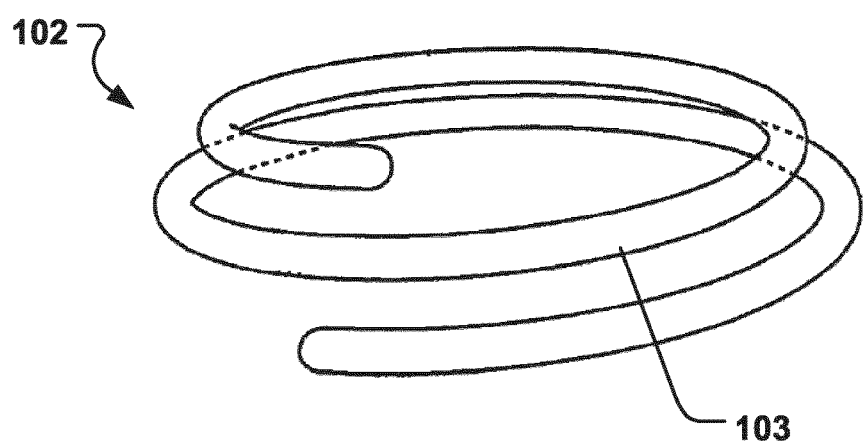
FIG. 2e is an illustration of a part of a medical system according to embodiments of the invention.

FIG. 2d shows a medical system 100 for treating a defective mitral valve (MV) having an annulus (A) according to an embodiment of the invention. The system comprises in combination a removable elongate displacement unit 101 and a annuloplasty device 102 for permanent fixation at the mitral valve. The displacement unit 101 is adapted for temporary insertion into the CS adjacent the MV, and it has a delivery state for delivery into the CS. In the delivery state, the displacement unit 101 is bendable in an arch shape at a portion of the displacement unit 101 upon said delivery, i.e. as it is positioned in the CS, and can therefore adapt to the anatomy of the CS and conform to the curvature of the CS adjacent a dilated MV, which is illustrated in FIG. 2b. As the displacement unit 101 is removable and adapted for temporary insertion in the CS, it may be permanently attached to a delivery unit 111, such as a delivery wire, guide wire or the like. The displacement unit 101 has further an activated state to which the displacement unit is temporarily and reversibly transferable from the delivery state. Thus, at least a portion of the displacement unit 101 is temporarily movable in a radial direction (r) of the CS towards the MV in such a manner that the shape of the annulus (A) is modified to a modified shape (A'), as the displacement unit 101 is transferred its activated state, which is illustrated in FIG. 2c. As the displacement unit is being able to move in the radial direction, efficient downsizing of the valve annulus is provided. Substantially the entire length of the displacement unit may be able to move in the radial direction. Alternatively, a portion such as a middle portion of the displacement unit positionable at the apex point 116 of the annulus curve is movable in the radial direction. This can provide for a more efficient and improved downsizing effect than prior art devices where only the radius of curvature of the device is changed. The annuloplasty device 102 is adapted for permanent fixation at the mitral valve annulus by annuloplasty of the valve when the modified shape (A') is obtained. Hence, the annuloplasty device 102 comprises a fixation structure 103 that is adapted to retain the modified shape (A'). FIG. 2e shows an example of such annuloplasty device 102, having a fixation structure in the form of loop structures 103 such as a helix-shaped loop structure for positioning on either side of the MV to retain the modified shape (A') of the annulus. The annuloplasty device 102 may be catheter deliverable, whereby it assumes an elongated shape when delivered trough a catheter and transferable to a looped structure when positioned at the MV.

Figure 2F:
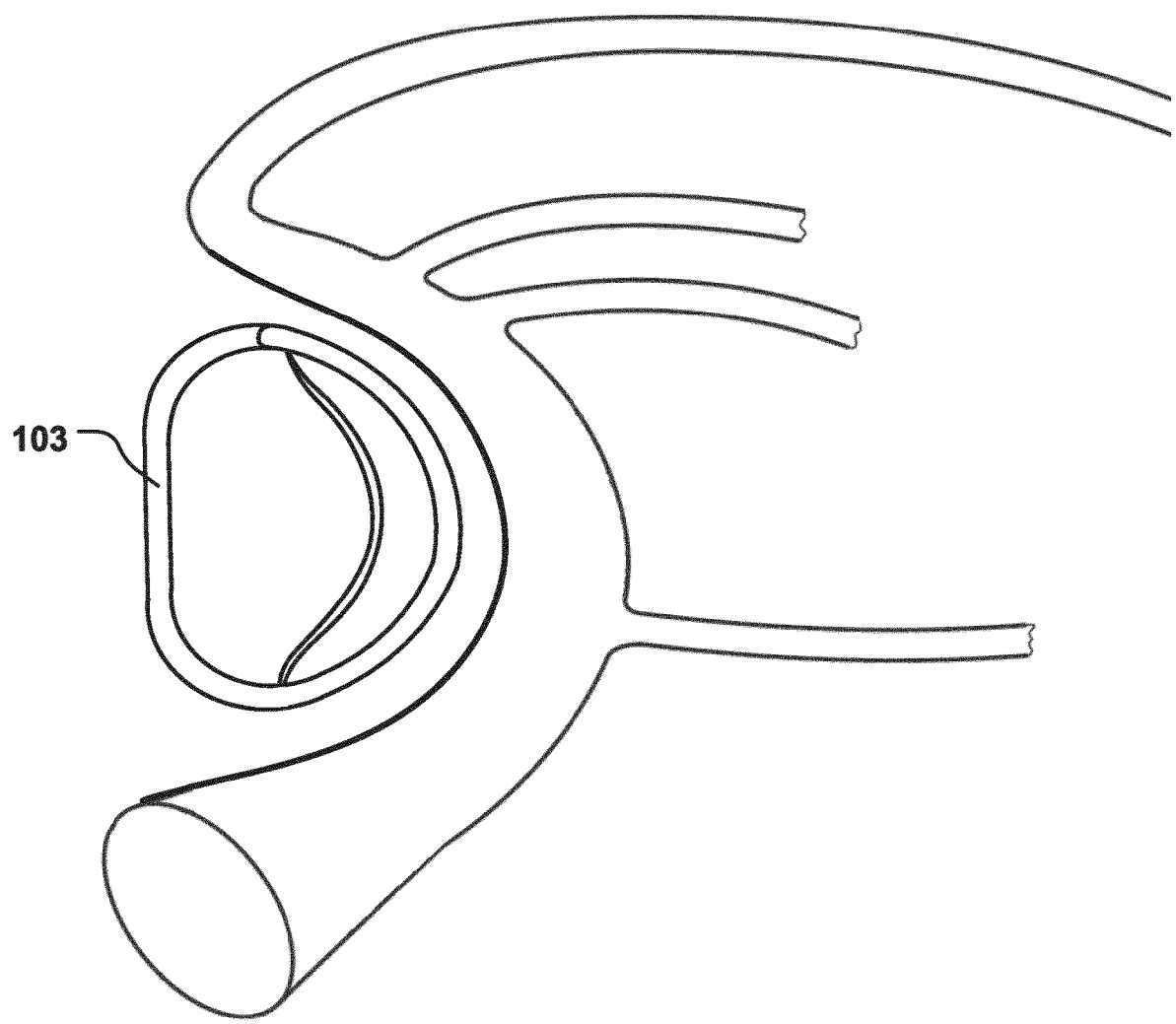
FIG. 2f is an illustration of a part of a medical system according to embodiments of the invention.

At least a portion of the loop structure 103 conforms to the curvature of the annulus. In FIG. 2d the annuloplasty device 102 is fixated at the annulus to retain the modified shape of the annulus and provide for closure of the dilated MV leaflets seen in FIG. 2a. This fixation of the previously dilated MV leaflets by the annuloplasty device 102 is accordingly facilitated and improved by the temporary downsizing of the annulus into the modified shape (A') by the displacement unit 101, which is subsequently withdrawn from the CS as illustrated in FIG. 2f. The medical system 100 therefore provides for efficient permanent fixation of defective MV leaflets via temporary modification or displacement of the MV geometry utilizing a removable displacement unit 101 in the CS and an annuloplasty device 102 for fixation of the temporary modification provided by the displacement unit 101. Since the displacement unit 101 is temporarily and reversibly transferable to the activated state, it may again be reversed to the delivery state, and removed from the CS. Long term negative effects of implants in the CS or the need for repositioning or modification of a CS implant to ensure proper long-term function may thereby be avoided. Implants that are traumatic to the CS, both after short-term or long-term use is also avoided. The medical system 100 in combination provides the synergetic effect of providing efficient temporary downsizing with the displacement unit 101 and fixation of the downsized annulus with the annuloplasty device 102 in the long-term. Since the displacement unit 101 is temporarily provided in the CS the downsizing can be made in a much more robust and efficient manner compared to an implant, since the CS is only affected for short period of time while the annuloplasty device 102 is fixated at the annulus. Once the annuloplasty device 102 is fixated the displacement unit 101 may be reversed to its delivery state and removed from the CS.

Hence, the fixation structure 103 may thus be adapted to retain the modified shape (A') of the annulus in the delivery state of the displacement unit 101 after temporary activation in the activated state.

At least a portion of the displacement unit 101 may be reversibly expandable in the radial direction (r) in the activated state. FIG. 2b illustrates the delivery state of the displacement unit 101 and FIG. 2c shows the activated state of the latter where the displacement unit 101 has been radially expanded to provide the movement in the radial direction (r) and the temporary downsizing as explained above.

Figure 3A:
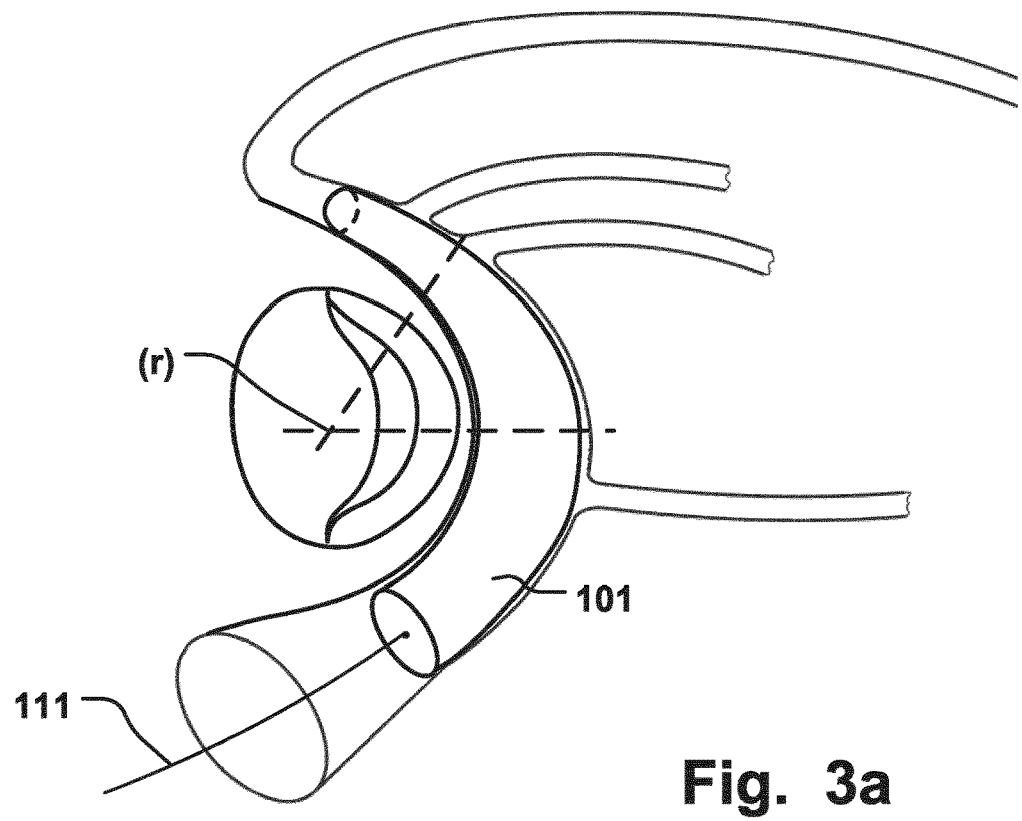
FIG. 3a is an illustration of a part of a medical system according to embodiments of the invention in a first state.
Figure 3B:
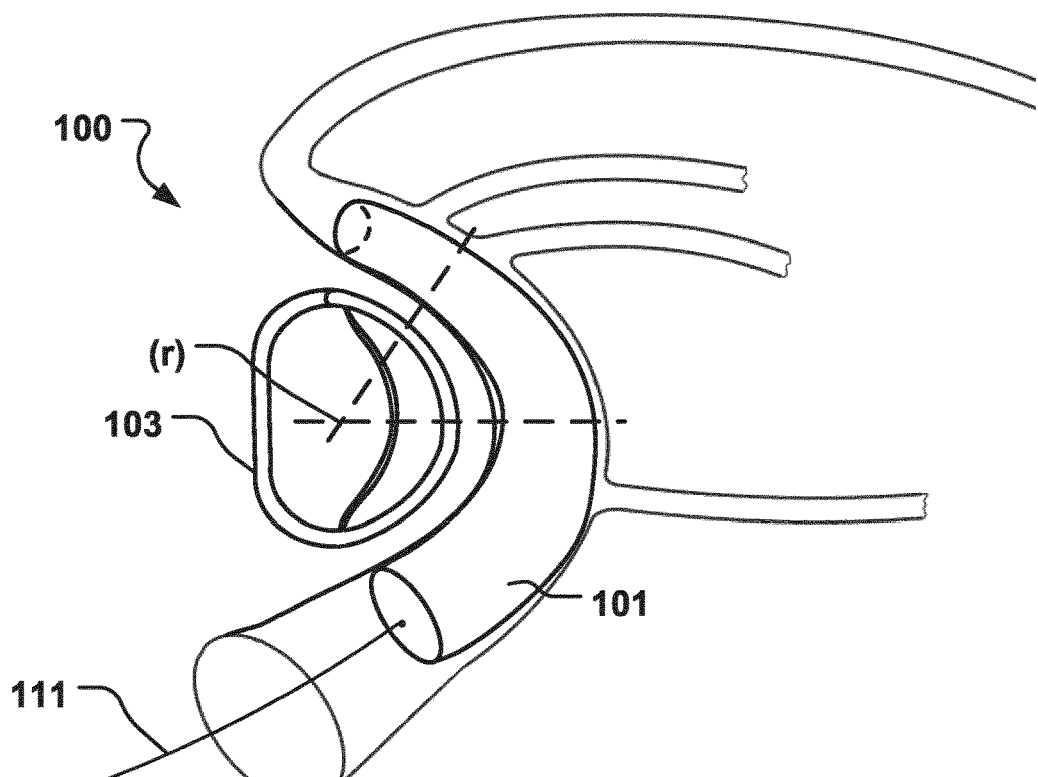
FIG. 3b is an illustration of a medical system according to embodiments of the invention.

Alternatively, or in addition, at least a portion of the displacement unit 101 may be reversibly foldable in the radial direction (r) in the activated state. FIG. 3a illustrates the delivery state of the displacement unit 101 and FIG. 3b shows the activated state of the latter where the displacement unit 101 has been folded, curved or bent in the radial direction (r) to provide movement of the annulus in the radial direction (r). This may provide for an improved downsizing as a greater portion of the annulus may be exerted to the force provided by the displacement unit 101.

At least a portion of the displacement unit may be reversibly movable to an activated shape [in said activated state] that at least partly assumes the curvature of said loop structure.

The displacement unit 101 may thus have a shape in the activated state that is customized, adapted, or conformable to the shape of the annuloplasty implant 102. For example, part of the curvature of the displacement unit 101 in the activated state may be equal to the curvature of the loop structure of the annuloplasty implant 102. It is thereby possible to obtain an efficient interplay and synergy between the functions of the displacement unit 101 and the annuloplasty implant 102 since the geometries are partly corresponding for an efficient downsizing into a modified shape of the annulus (A') that can be fixated by the annuloplasty implant 102 having a corresponding shape.

The displacement unit may comprise a lumen 105 the in the axial direction 106 of the displacement unit 101, which is illustrated in FIGS. 4a-b, FIGS. 5a-b, and FIG. 6. It may be desirable improve the blood flow in the CS while the displacement unit 101 is inserted in certain situations, hence the lumen may allow a blood flow there through. The lumen 105 may allow insertion of guide wires or the like through the displacement unit 101, and further it may allow actuating units disposed in the interior of the displacement unit 101 to control the shape or size in any parts of the displacement unit 101, to improve the control of the temporary downsizing procedure.

Figure 4A:
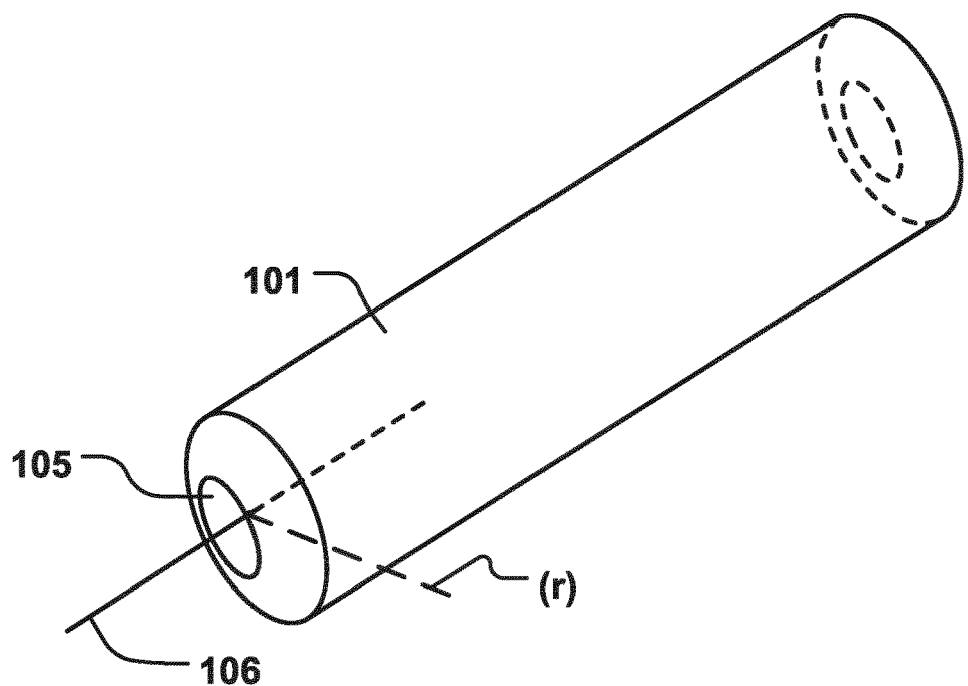
FIG. 4a is an illustration of a part of a medical system according to embodiments of the invention in a perspective view.
Figure 4B:
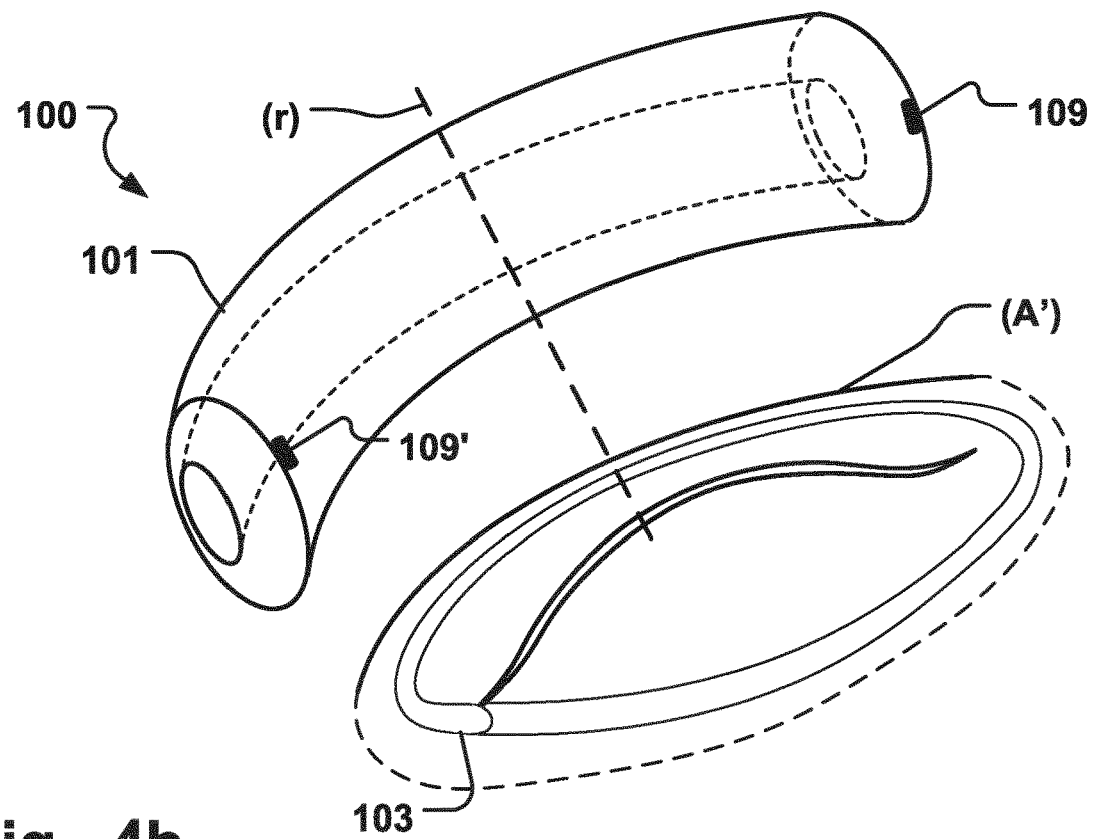
FIG. 4b is an illustration of a medical system according to embodiments of the invention in a perspective view.

The displacement unit 101 may comprise at least one inflatable unit 104 such as a balloon that is actively and reversibly expandable to a set shape. An inflatable unit 104 provided at a middle portion of the displacement unit that is positioned at the apex point 116 of the annulus curve, or having a length corresponding to the portion of the CS extending along annulus of the valve, provides for radial movement along this portion, by inflating the balloon. This can provide for a more efficient and improved downsizing effect than prior art devices where only the radius of curvature of the device is changed, or where a balloon is provided at a distal end point for the purpose of anchoring only. Control of the geometry of the displacement unit 101 is thereby provided, such that it can be transferred to the activated state in a controlled manner with a desired geometrical configuration as a set shape, and thereby achieve a desired form of the modified shape (A') of the MV annulus. An arrangement of fluid ports (not shown) may be disposed in the interior of the displacement unit 101 to its control inflation in a desired manner. For instance, the inflatable unit 104 may assume a preset curved shape in the activated state of the displacement unit 101, such that it conforms more to the shape of the annulus. I.e. besides the bendable properties of the displacement unit 101 when inserted in the CS in the delivery state, it may be actively folded, curved or bent into a shape with a further reduced radius of curvature when transferred into the activated shape, as discussed further below in relation to FIGS. 9a-b, and FIGS. 11a-c. Further, as seen in FIG. 4b the displacement unit 101 assumes a curved shape that is bending around the posterior side of the annulus, and as mentioned above, the displacement unit 101 may assume a preset curved shape in the activated state to further decrease the radius of curvature and improve the downsizing effect.

Figure 5A:
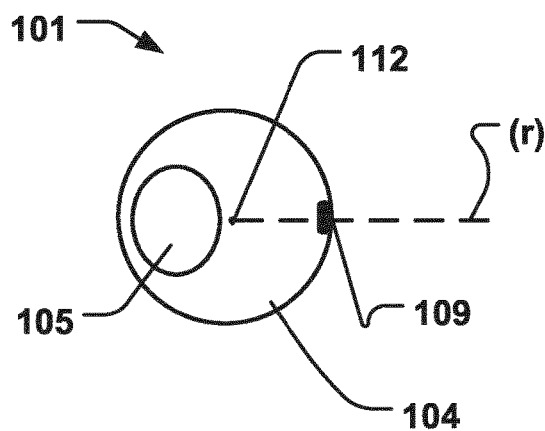
FIGS. 5a-b are illustrations of a part of a medical system according to embodiments of the invention in a side views.
Figure 5B:
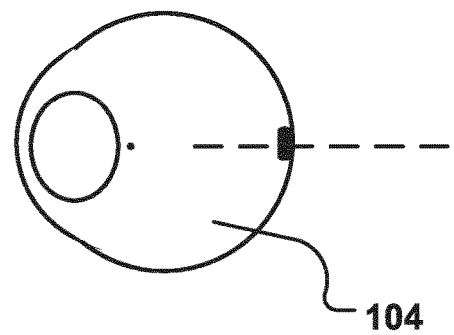
Figure 8A:
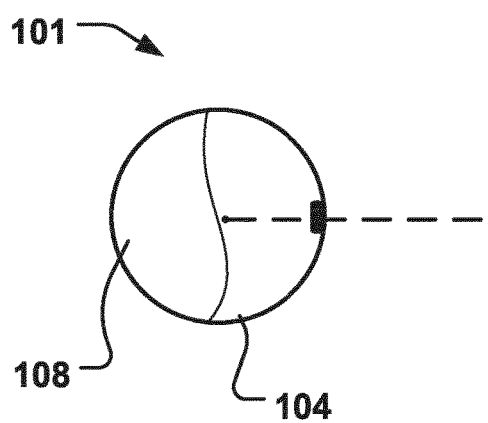
FIGS. 8a-b are illustrations of a part of a medical system according to embodiments of the invention in a side views.

The inflatable unit 104 may be asymmetrically expandable in the radial direction (r) of the CS. The cross-section of such inflatable unit 104 is illustrated in FIGS. 5a-b, and FIGS. 8a-b, where the radial portions of the inflatable unit 104 expand to different degrees, hence asymmetrically, in the activated state. For instance, the radial portion of the cross-section to the right in the figures, assumes an increased cross-section in the activated state (FIG. 5b, FIG. 8b), whereas the left portion has not expanded or expanded to a lesser degree, see e.g. left portion 108 compared to right portion 104 in FIG. 8b in the activated state versus the delivery state (FIG. 8a). Asymmetric expansion may improve the downsizing effect in the radial direction (r) of the inflatable unit 104 that is positioned closest to the posterior side of the annulus, i.e. in the radial direction of the CS. The asymmetric expansion may be provided by having portions of the inflatable unit 104 of different material properties such as different expansion capabilities, or by arranging the inflatable unit 104 asymmetrically with respect to a center portion of the displacement unit 101. In FIGS. 5a-b a lumen 105 is arranged asymmetrically with respect to such center point 112, i.e. rotational asymmetry, that may provide for a directed expansion of the inflatable unit 104 in a set direction such as in the radial direction of the CS.

Figure 11A:
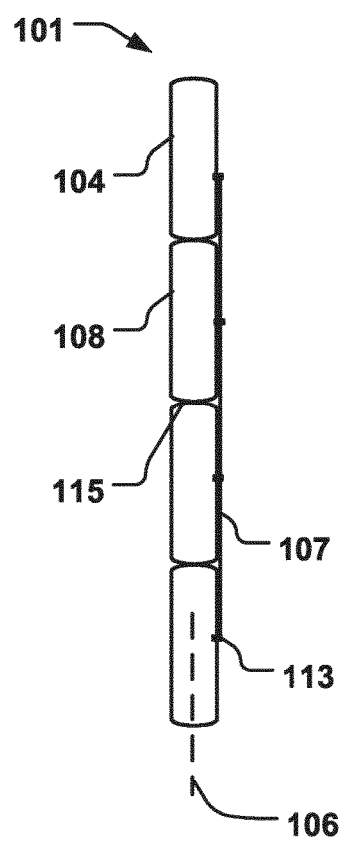
FIGS. 11a-c are illustrations of a part of a medical system according to embodiments of the invention in a top-down view.
Figure 11B:
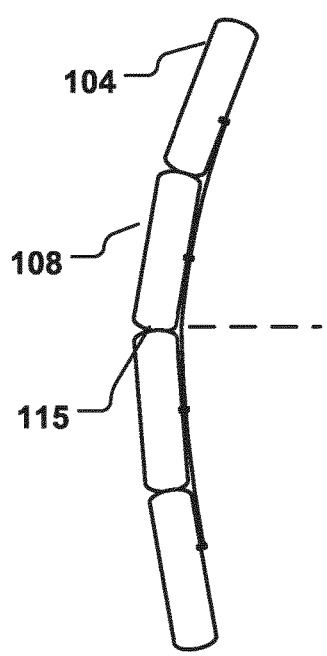
Figure 11C:
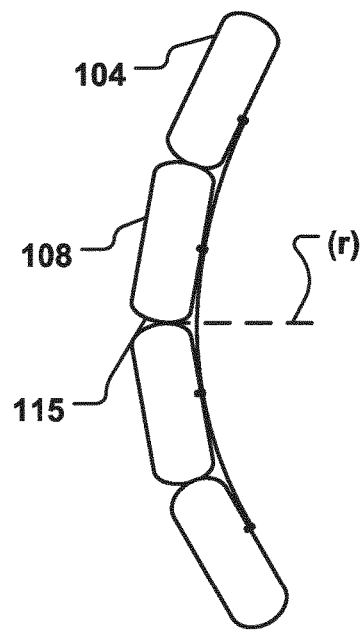

Reference is now made to FIGS. 9a-b. The inflatable unit 104 may assume a folded or curved shape when expanded in the activated state. As mentioned this may improve the downsizing further by exerting a force around the periphery of the MV at the annulus. In addition, or alternatively to having the inflatable unit 104 to assume a preset shape when expanded the displacement unit may comprise a restraining member 107 that is arranged to restrict movement of the inflatable unit in at least one direction when expanded from the delivery state. The restraining member 107 may accordingly steer the shape of the displacement unit 101 even further by limiting expansion or folding in certain directions. For instance, the restraining member 107 may limit expansion at a first longitudinal side of the inflatable unit 104 so that during expansion of the inflatable unit 104 in the longitudinal direction 106, a second side that may be opposite the first side, that is not restrained, will expand to a larger degree than the first side and the inflatable unit 104 will fold in the direction of the first side since these sides of the inflatable unit 104 will assume different lengths. FIG. 9b shows folding in this manner, and in the radial direction of the CS. The restraining member 107 may thus be flexible, and may be affixed to various parts of the displacement unit 101 in order to achieve the desired shape, such as along a longitudinal side at with fixation means 113. FIGS. 11a-c shows another example of the displacement unit 101 that may assume a folded or curved shape when expanded in the activated state by controlling movement of a first portion of the displacement unit 101 with a restraining member 107, such that a second portion moves to a different extent, or along a different path, than the first portion.

Figure 7:
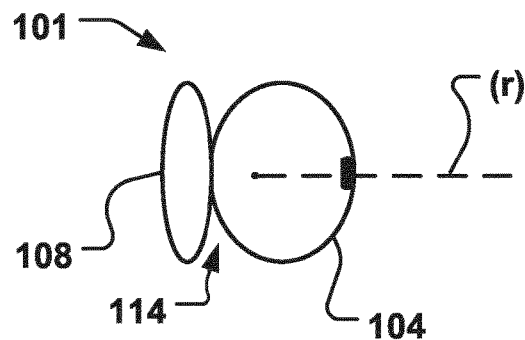
FIG. 7 is an illustration of a part of a medical system according to an embodiment of the invention in a side view.
Figure 8B:
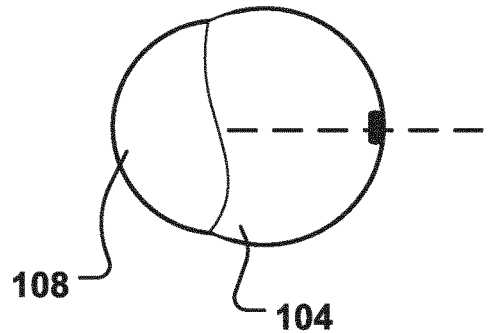

The at least one inflatable unit 104 may comprise a plurality of inflatable units wherein a first inflatable unit 104 and a second inflatable unit 108 are independently and reversibly inflatable. FIG. 10a shows a displacement unit 101 that comprises first and second inflatable units 104, 108, that can be expanded independently and to different sizes in the activated state, as seen in FIG. 10b. It is thereby possible to vary the force by which the displacement unit 101 exerts on the CS along the length of the displacement unit 101 to achieve a desired modification of the MV annulus and corresponding modification of the MV leaflets. FIG. 7 and FIGS. 8a-b illustrate embodiments where the displacement unit 101 comprises first and second inflatable units 104, 108, along the radial direction (r) of the displacement unit 101. It may thus be possible to control the amount of expansion in the radial direction and achieve asymmetric radial expansion as discussed above. Further, a passage 114 may be provided along the axial direction 106 between the first and second inflatable units 104, 108, as seen in FIG. 7.

FIGS. 11a-c illustrates a displacement unit 101 having first and second inflatable units 104, 108, along the axial direction 106, and a restraining member 107 at a first portion thereof for controlling movement in the activated state as explained above in relation to FIGS. 9a-b. The displacement unit 101 may assume the shape illustrated in FIG. 11b when in the delivery state and positioned in the CS adjacent the MV. In this state the first and second inflatable units 104, 108, have been displaced in relation to each other in order to easily conform to the CS anatomy. The first and second inflatable units 104, 108, may be displaced at their joining ends 115, or in another manner that allows adapting to the shape of the CS. In FIG. 11c the first and second inflatable units 104, 108, have assumed an altered shape in the activated state. Due to the altered shape of each of the inflatable units 104, 108, they have been displaced in relation to each other at a second portion of the displacement unit 101, that is not restrained by the restraining member 107. The displacement unit 101 thereby exhibits a further modified shape in the activated state as the restraining member 107 limits movement of the inflatable units 104, 108, at a portion thereof. This may provide for improving the downsizing effect of the MV. The restraining member 107 may be arranged along a first side of the displacement unit 101, attaching and joining each of the first and second inflatable units 104, 108, at a first side thereof, and the first and second inflatable units 104, 108, may each assumed an increased axial extension in the activated state such that they are axially displaced at their joining ends 115. Such axial displacement may thus be restricted at the first side due to the fixation of the first and second inflatable units 104, 108, by the restraining member 107. Unrestricted axial expansion at a second side, radially opposite the first side may thus provided for a further folded shape in the activated state.

The displacement unit may comprise, at a radial portion thereof, at least one radiopaque marker 109, 109', for rotational alignment of the displacement unit in the CS, which is seen in FIG. 4b, and further in FIGS. 5a-b, 6, 7, 8a-b.

Figure 6:
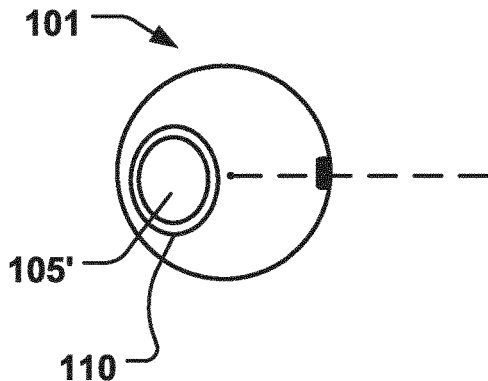
FIG. 6 is an illustration of a part of a medical system according to an embodiment of the invention in a side view.

The displacement unit 101 may further comprise a support structure 110 arranged to support movement of the displacement unit 101 in the radial direction (r) and/or support a passageway 105' through the displacement unit 101 in the axial direction 106, as seen in FIG. 6. The support structure may 110 be a framework or a braided structure.

A Method 200 for treating a defective mitral valve (V) having an annulus (A) according to one embodiment of the invention is illustrated in FIG. 12. The method comprises inserting 201 a removable elongate displacement unit 101, which may have any combination of the features described according to the disclosure as described above in relation to FIGS. 1-11, in a delivery state into a coronary sinus (CS) adjacent the valve; activating 202 the displacement unit 101 in an activated state whereby at least a portion of the displacement unit 101 is moved in a radial direction (r) of the CS towards the valve in such a manner that the shape of the annulus is modified to a modified shape (A'); fixating 203 an annuloplasty device 102 at the mitral valve annulus when the modified shape is obtained, whereby the annuloplasty device 102 comprises a fixation structure 103 that is adapted to retain the modified shape; and removing 204 the elongate displacement unit 101 after temporary activation in the activated state.

Figure 13A:
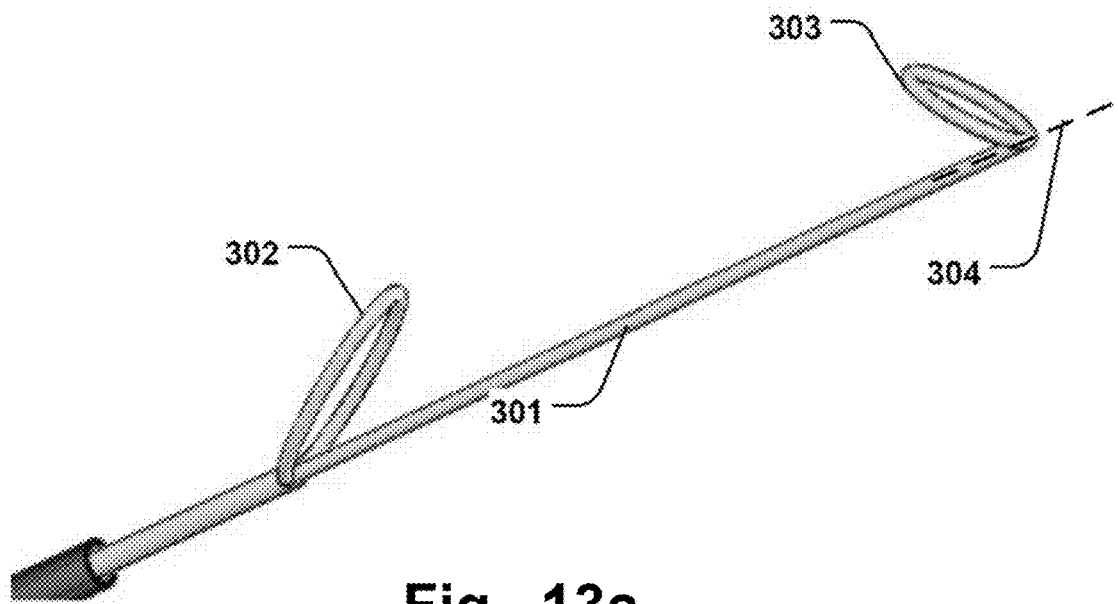
FIGS. 13a-c are illustrations of a displacement unit according to embodiments of the invention, also being part of a medical system according to embodiments of the invention.
Figure 13B:
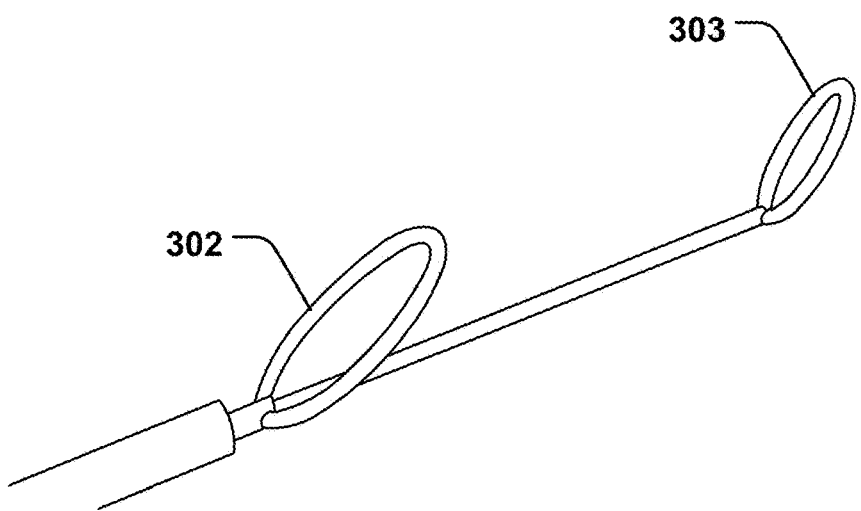
Figure 13C:
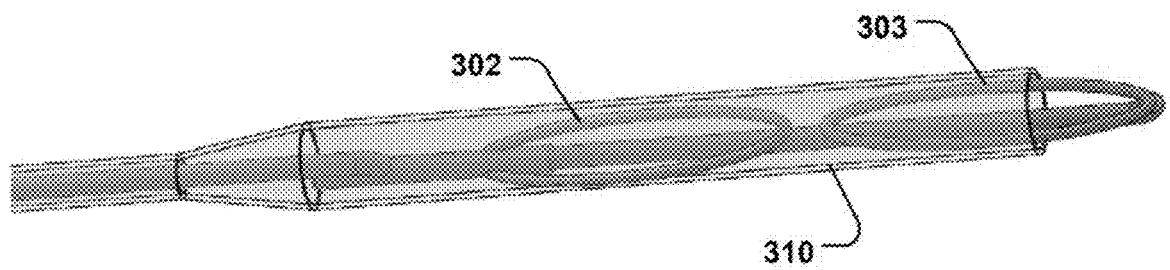
Figure 14A:
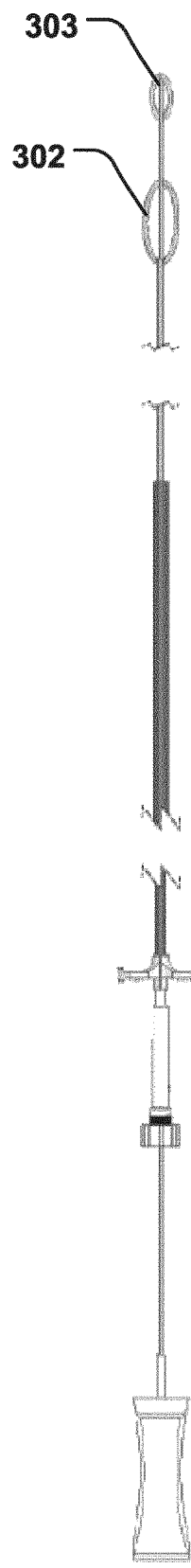
FIGS. 14a-b are illustrations of a displacement unit according to embodiments of the invention, also being part of a medical system according to embodiments of the invention.
Figure 14B:
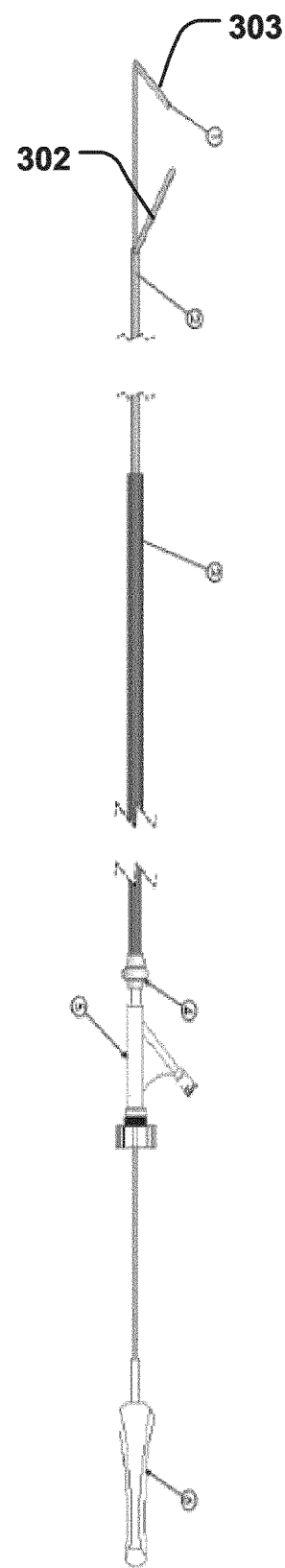
Figure 15:
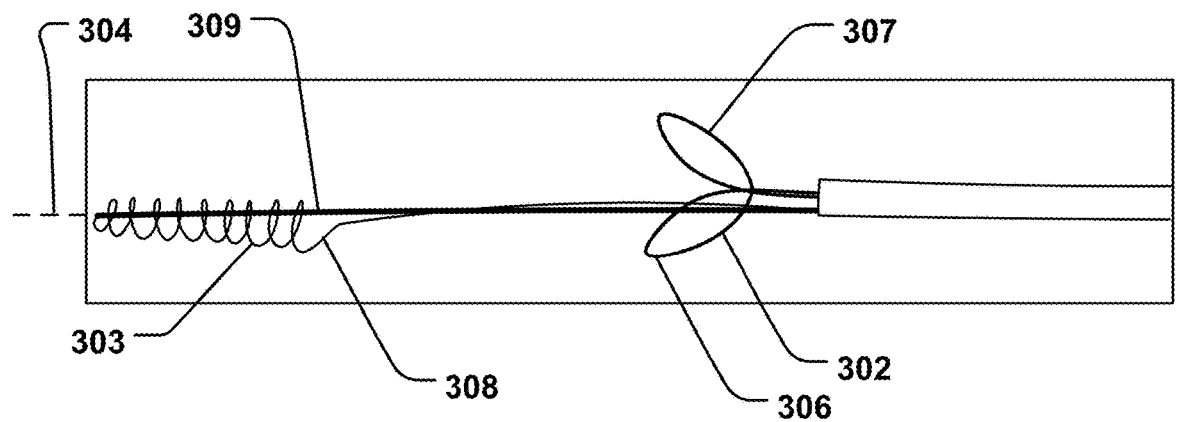
FIG. 15 is an illustration of a displacement unit according to embodiments of the invention, also being part of a medical system according to embodiments of the invention.
Figure 16:
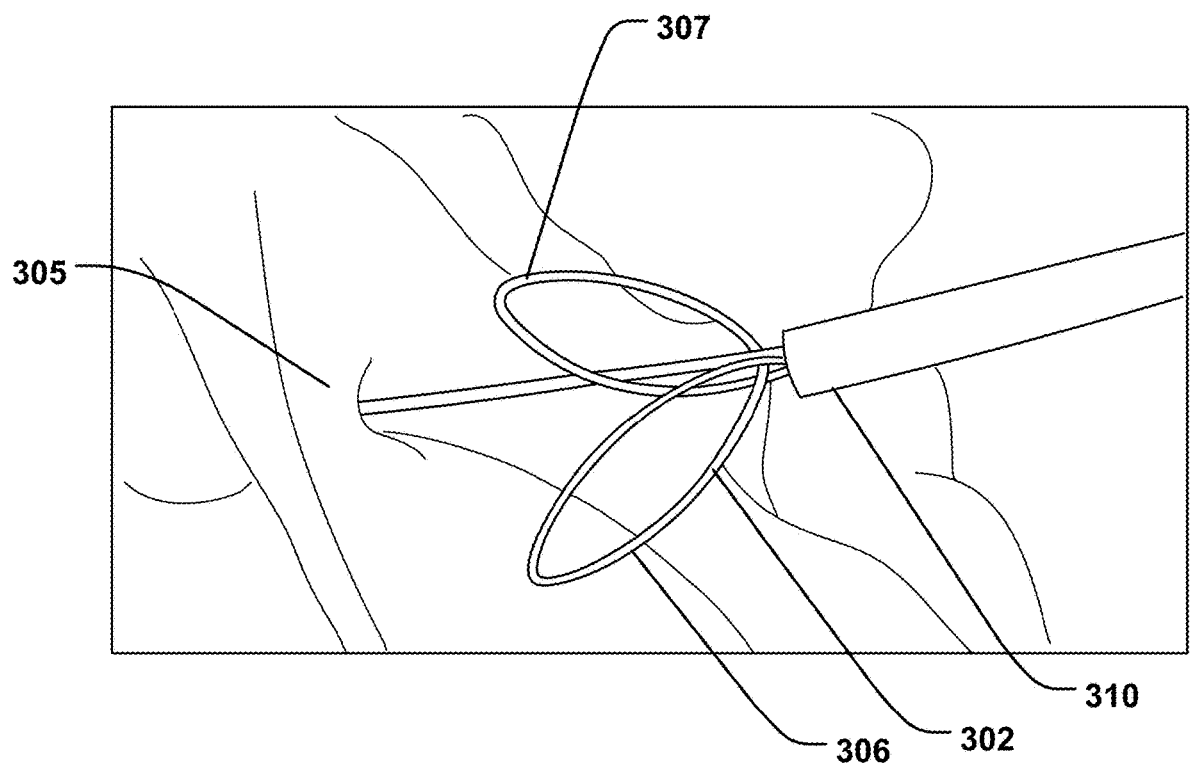
FIG. 16 is an illustration of a displacement unit according to embodiments of the invention, in use, also being part of a medical system according to embodiments of the invention.
Figure 17A:
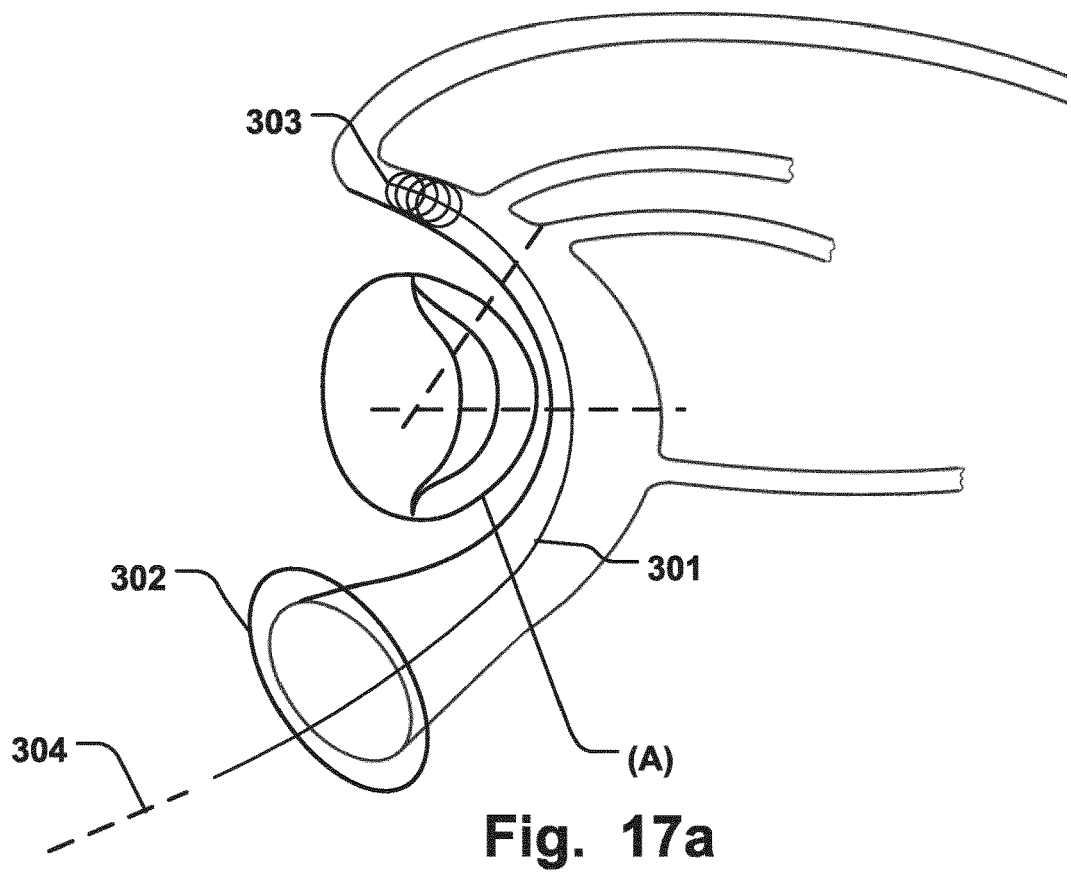
FIG. 17a is an illustration of a displacement unit according to embodiments of the invention, also being part of a medical system according to embodiments of the invention.
Figure 17B:
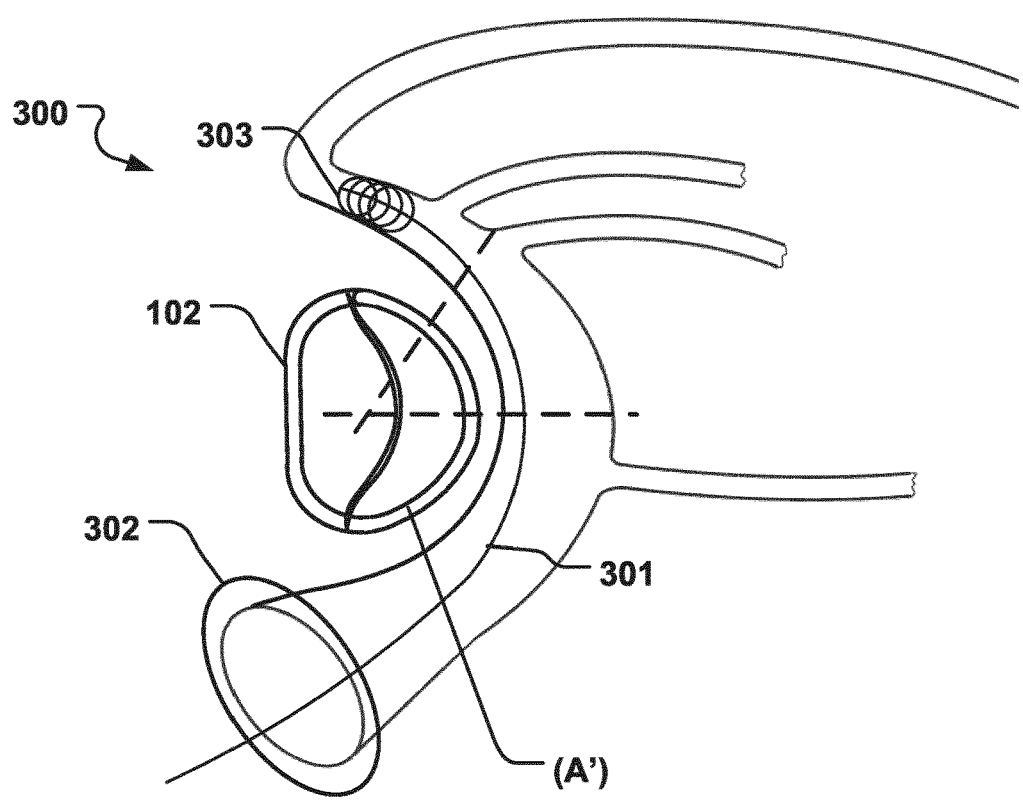
FIG. 17b is an illustration of a medical system according to embodiments of the invention.
Figure 18A:
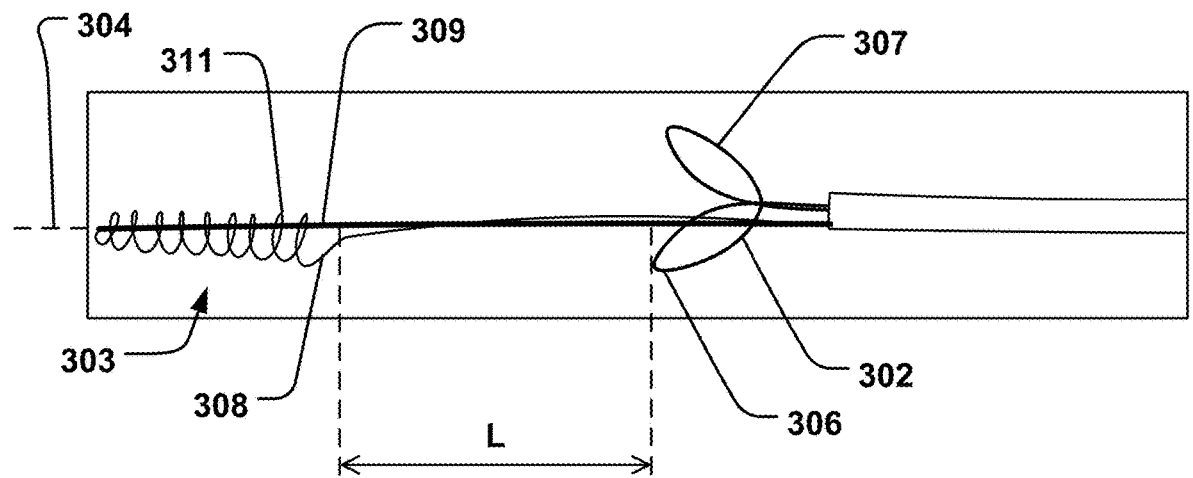
FIGS. 18a-b are illustrations of a displacement unit according to embodiments of the invention, also being part of a medical system according to embodiments of the invention.
Figure 18B:
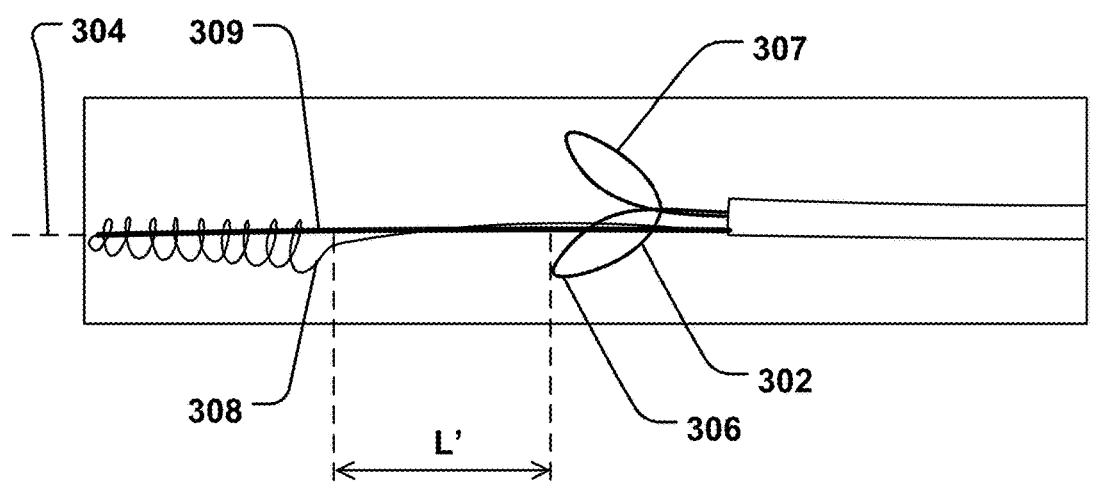

FIG. 17b show a medical system 300 for treating a defective mitral valve (MV) having an annulus (A). The system 300 comprises in combination a removable and flexible elongate displacement unit 301 for temporary insertion into a coronary sinus (CS) adjacent the valve, wherein the displacement unit has a delivery state (FIG. 17a) for delivery into said CS, and an activated state to which the displacement unit is temporarily and reversibly transferable from the delivery state. The displacement unit comprises a proximal reversibly expandable portion 302, a distal anchoring portion 303 being movable in relation to the proximal expandable portion in a longitudinal direction 304 of the displacement unit (so that the distance (L) between the two portions 302, 303, is reduced as seen in FIGS. 18a-b) to the activated state in which the shape of the annulus is modified to a modified shape (A') (FIG. 17b); and an annuloplasty device 102 for permanent fixation at the mitral valve annulus by annuloplasty of the valve when the modified shape is obtained (FIG. 17b). The annuloplasty device 102 comprises a fixation structure 103 that is adapted to retain the modified shape. By moving the distal anchoring portion 303 in the longitudinal direction towards the proximal expandable portion 302 the radius of curvature of the CS and also the valve annulus can be reduced. The modified shape of the annulus is then fixated by the annuloplasty device 102, before removing the displacement unit 101. Previous prior art devices for insertion into the CS are for permanent implantation and are not adapted to be removed or used in conjunction with an annuloplasty device 102. Alternatively, the prior art devices are focused bending of a segmented device only. The combination of reducing the length of the displacement unit 301 and having a proximal expandable portion 302 that efficiently provides a counter force against the anchoring portion 303, greatly improves the downsizing effect. Absence of a proximal expandable portion will make the downsizing considerably more difficult. The system 300 allows for improved efficiency treating diseased valves due to efficient downsizing of the valve via the CS and subsequent fixation of the annulus at the valve itself. Both the proximal expandable portion 302 and the distal anchoring portion 303 are reversibly expandable for delivery and retrieval from a sheath 310, see FIG. 13c. In one embodiment the distal anchoring portion 303 and/or the proximal expandable portion 302 may pivot towards the longitudinal direction 304 in order to be easily retracted into the sheath 310, see FIG. 13b. FIGS. 14a-b shows the catheter with the displacement unit 101 at the distal end to be inserted into the CS. Another embodiment is shown in FIGS. 15 and 16. The distal anchor is inserted and fixated into the CS and the proximal reversibly expandable portion 302 folds out from the sheath 310 to allow for performing the downsizing and is then folded back into the sheath 310 and is retracted.

The fixation structure 102 is adapted to retain the modified shape of the annulus in the delivery state of the displacement unit after temporary activation in the activated state.

The distance (L) between the proximal expandable portion 302 and the distal anchoring portion 303 in the longitudinal direction 304 decreases to a reduced distance (L') when the displacement unit 301 is transferred from the delivery state to the activated state, see FIGS. 18a-b. Since the distal anchoring portion 303 is fixated in the CS decreasing the distance between the proximal expandable portion 302 and the distal anchoring portion 303 will result in a reduced radius of curvature of the CS which will downsize the valve. Thus, the radius of curvature of the displacement unit 301 decreases when the displacement unit is transferred from the delivery state to the activated state.

The proximal expandable portion 302 may be reversibly foldable to an expanded state for positioning against a tissue wall 305 at the entrance of the CS, as shown in FIG. 16. This provides for a very stable fixation of the position of the proximal expandable portion 302 relative the distal anchor 303 for improved control of the downsizing of the valve. Since the proximal expandable portion 302 may be shaped and adapted for positioning against the tissue wall 305 at the entrance of the CS, and not inside the CS itself it also reduces the risk of damaging the CS. Also, since the proximal expandable portion 302 is positioned outside the CS it is not constrained by the size of the CS and can thus be reversibly expanded to a diameter that spreads the force over a larger portion, thus reducing the pressure on the tissue. This also reduces risk of damages.

The proximal expandable portion 302 may comprise expandable wire lobes 306, 307, for positioning against the tissue wall 305 at the entrance of the CS, see FIG. 15-16. The wires lobes are adapted to be fixated against the tissue wall outside the CS, and provide for a stable fixation point. The wire lobes 306, 307 may expand on either side of the sheath 310 to spread the force symmetrically for controlled positioning. Any expandable structure such as a balloon etc. may be provided as proximal expandable portion 302 for reversible expansion against the tissue wall 305 at the entrance of the CS, i.e. outside the CS to provide the above mentioned advantages.

The proximal expandable portion 302 may have a larger expanded diameter than the distal anchoring portion 303 in the activated state of the displacement unit 301. This is e.g. illustrated in FIG. 15, and allows the proximal expandable portion 302 to be more securely positioned in relation to the anchor 303 for a more controlled downsizing.

The distal anchoring portion 303 is expandable to anchor against said CS in the activated state of the displacement unit 301. It provides sufficient force against the CS to be fixated relative the proximal expandable portion 302 when pulling the distal anchoring portion 303 towards the proximal expandable portion 302.

The distal anchoring portion 303 may comprise an expandable coiled wire 311, see FIG. 15. The coiled wire provides for efficient fixation against the CS, since pressure is provided evenly and circumferentially along the length of the coil, while at the same times allows to be easily retracted into the sheath 310 by extending the coil in the longitudinal direction 304. The coiled wire may be connected to a control wire 308, FIG. 15, which is adapted to stretch the distal anchoring portion to a reduced diameter delivery shape, and reduce tension on the coiled wire in the activated state to expand the distal anchoring portion. Hence, it also allows for easy deployment of the distal anchor in the CS by reducing the tension on the coil so that it can be retracted and expanded in diameter for fixation against the CS. Further, the coil 311 provides for keeping the body lumen open so that blood flow can be maintained.

The displacement unit 301 may comprise a delivery wire 309, FIGS. 15 and 18a-b, adapted to deliver the distal anchoring portion 303 and to pull the distal anchoring portion 303 towards the proximal expandable portion 302 in the activated state, whereby the distance (L) between the two is reduced to the shorter distance (L'), as illustrated in FIGS. 18a-b, to provide the downsizing. The control wire 308 for the anchoring portion 303 may be pulled simultaneously and with the same displacement so that the anchoring portion maintains its length in the longitudinal direction 304.

The proximal expandable portion 303 may be reversibly foldable to an expanded state where the proximal expandable portion 303 has a diameter substantially larger than the diameter of the CS. This allows for a more stable fixation outside the CS with the advantages mentioned above.

Figure 19A:
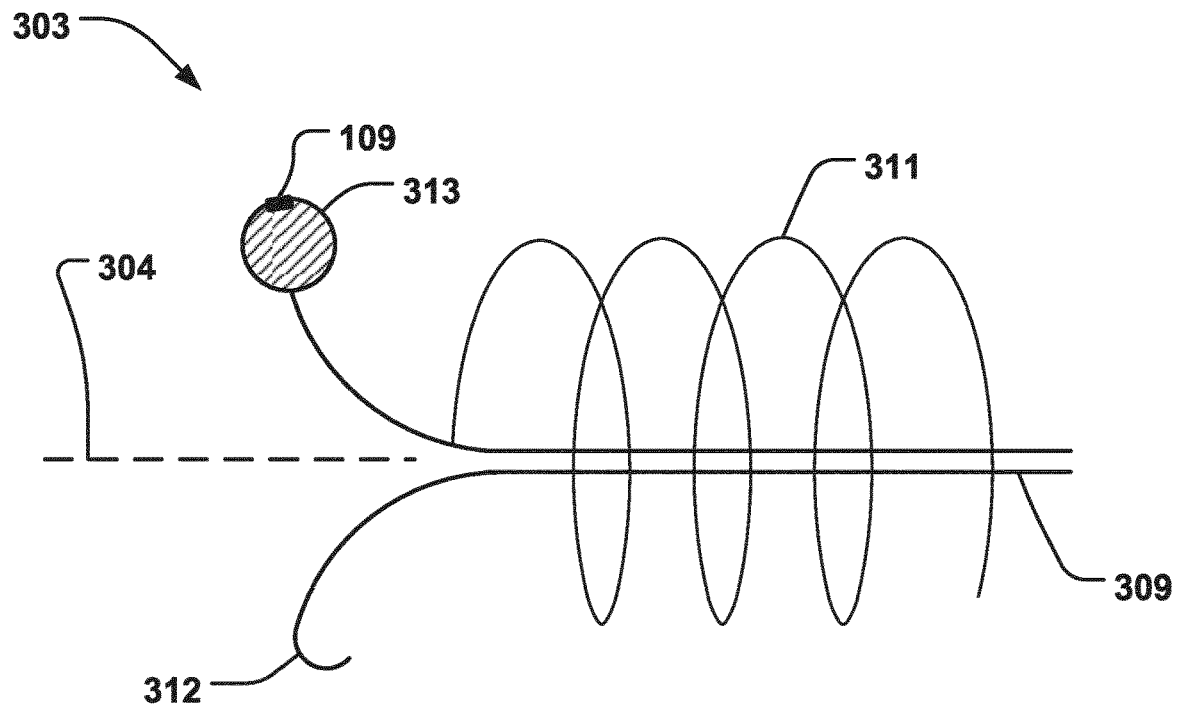
FIGS. 19a-b are illustrations of a displacement unit according to embodiments of the invention, also being part of a medical system according to embodiments of the invention.
Figure 19B:
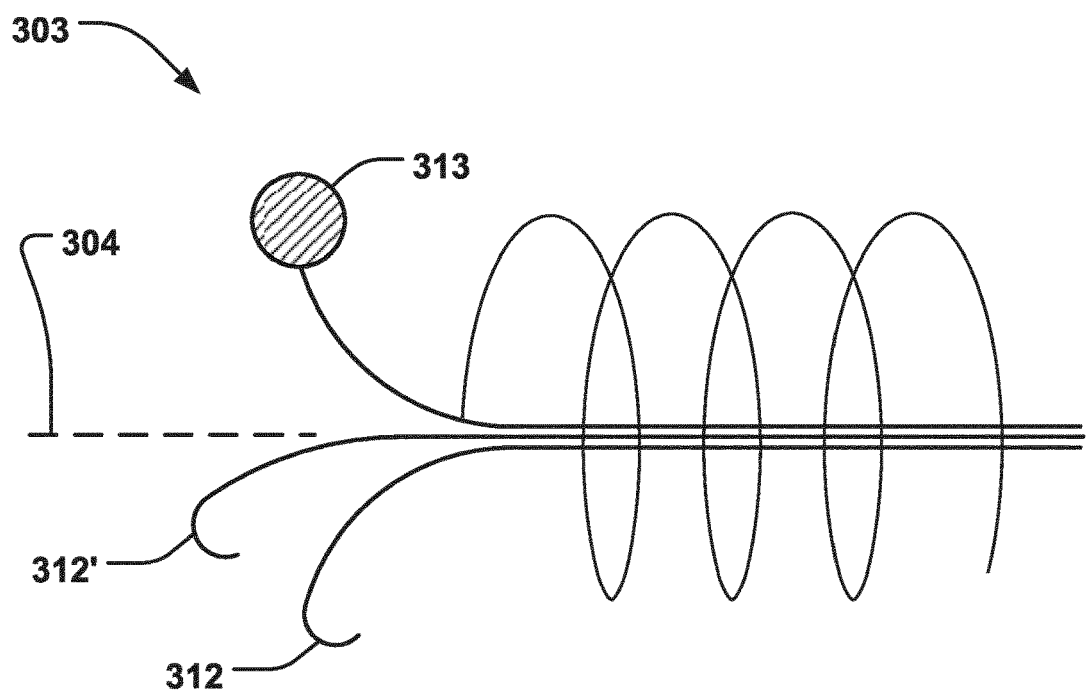

The anchoring portion may comprise a tissue retention portion such as at least one hook 312, 312', as illustrated in FIGS. 19a-b. The tissue retention portion 312, 312', provides for efficient fixation of the anchoring portion 303 inside the CS, that allow for efficient downsizing of the valve annulus. FIG. 19b illustrates the case when to retention portions 312, 312', are employed, but any number of retention portions can be used, to optimize the efficiency of the procedure. In addition to hooks, other retention members grasping the tissue can be provided. The retention portions 312, 312', are preferably oriented towards the myocardial wall of the CS which is more robust for grasping of the retention portions 312, 312'.

The anchoring portion 303 may comprise a tissue apposition portion 313 having a tissue atraumatic surface, such as an at least partly curved or spherical surface. The tissue apposition portion 313 provides for exerting a counter force against the wall of the CS, stabilizing the anchoring portion 303, and allowing for the retention portion 312, 312', to more efficiently grasp the tissue and anchor against the same. Also, it helps keeping the CS vein open for sustaining a flow of blood, in addition to the coil 311 which also keeps the CS vein open. By having a tissue atraumatic surface, the tissue apposition portion 313 enhance the anchoring ability while at the same time reducing the risk of tissue damage to the wall of the CS. FIGS. 19a-b illustrates a spherical surface of the apposition portion, but it may have surface that lies smooth against the CS.

The tissue retention portion 312, 312', is expandable in a direction substantially perpendicular to the longitudinal direction 304. It may therefore efficiently engage the wall of the CS. For example, the retention portion 312, 312', can be formed of a metal alloy having a heat set shape where it assumes an outwardly curved shape as illustrated in FIGS. 19a-b, for engaging the tissue. The retention portion 312, 312', may be connected to the delivery wire 309, such that when the delivery wire is pulled back relative the proximal expandable portion 302, the retention portion 312, 312', grasp the tissue, anchors the anchoring portion 303, and draw the tissue against the proximal expandable portion 302 to achieve the reduced length (L') and the downsizing effect. Alternatively, or in addition, the retention portion 312, 312', may be connected to a separate control wire (not shown) so that the radially outward expansion of the retention portion 312, 312', can be controlled independently of the position of the delivery wire 309. Thus, the retention portion 312, 312', may first be retracted, e.g. within the coil 311, before pushed in the longitudinal direction 304, where it may assume the heat set radially expanded shape for grasping the tissue as discussed.

The tissue apposition portion 313 may be controlled and deployed in the same manner as described in the preceding paragraph for the retention portion 312, 312', e.g. being connected to delivery wire 309 or a separate control wire (not shown), such that the tissue apposition portion can be expandable in a direction substantially perpendicular to the longitudinal direction 304 for contacting the all of the CS.

The tissue retention portion and said tissue apposition portion may be expandable in substantially opposite directions, as illustrated in FIGS. 19a-b. This allows the tissue apposition portion 313 to provide a good counter force relative the retention portion 312, 312', for efficient grasping of the tissue and secure anchoring. Also, while the retention portion 312, 312', is directed to the stronger myocardial wall, the tissue apposition portion 313 is placed against the more sensitive side of the CS.

The displacement unit may comprise, at a radial portion thereof, at least one radiopaque marker 109 for rotational alignment of the displacement unit in the CS. E.g. the tissue apposition portion 313 may have a radiopaque marker 109 for assisting in orienting away from the myocardial wall. Alternatively, or in addition the retention portion 312, 312', may comprise a radiopaque marker 109.

FIG. 20 illustrates a method 400 for treating a defective mitral valve (V) having an annulus (A) comprising; inserting 401 a flexible and removable elongate displacement unit 301 in a delivery state into a coronary sinus (CS) adjacent the valve, positioning 402 a proximal expandable portion 302 against a tissue wall 305 at the entrance of the CS, positioning 403 a distal anchoring portion 303 inside the CS, activating 404 the displacement unit in an activated state whereby the distal anchoring portion is moved in a longitudinal direction 304 of the displacement unit to reduce the distance between the distal anchoring portion and the proximal expandable portion such that the shape of the annulus is modified to a modified shape (A'),
fixating 405 an annuloplasty device 102 at the mitral valve annulus when the modified shape is obtained, whereby the annuloplasty device comprises a fixation structure 103 that is adapted to retain the modified shape, removing 406 the elongate displacement unit after temporary activation in the activated state.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical system for treating a defective mitral valve having an annulus, said system comprising in combination:
    a removable and flexible elongate displacement unit for temporary insertion into a coronary sinus adjacent said valve, wherein said displacement unit has
    a delivery state for delivery into said coronary sinus, and
    an activated state to which the displacement unit is temporarily and reversibly transferable from said delivery state, said displacement unit comprises
        a proximal reversibly expandable portion,
        a distal anchoring portion being movable in relation to said proximal expandable portion along a longitudinal axis of said displacement unit to said activated state in which the shape of the annulus is modified to a modified shape; and
    an annuloplasty device for permanent fixation at the mitral valve annulus by annuloplasty of the valve when said modified shape is obtained, wherein said annuloplasty device comprises a fixation structure that is adapted to retain said modified shape wherein the proximal expandable portion comprises first and second expandable loops, wherein in the delivery state said proximal expandable portion is compressed within a sheath, and the first and second loops are folded such as to be parallel with the longitudinal axis, and wherein in the activated state said proximal expandable portion is expanded, out of the sheath, wherein the first and second loops pivot away from the longitudinal axis in opposite directions from one another for positioning against a tissue wall outside the entrance of said coronary sinus for providing a counter force against said distal anchoring portion.

2. The medical system according to claim 1, wherein said fixation structure is adapted to retain said modified shape of the annulus in the delivery state of the displacement unit after temporary activation in the activated state.

3. The medical system according to claim 1, wherein a distance between said proximal expandable portion and said distal anchoring portion in said longitudinal direction decreases to a reduced distance when said displacement unit is transferred from said delivery state to said activated state.

4. The medical system according to claim 3, wherein said displacement unit comprises a delivery wire adapted to deliver said distal anchoring portion and to pull said distal anchoring portion towards said proximal expandable portion in said activated state, whereby said distance is reduced.

5. The medical system according to claim 1, wherein a radius of curvature of said displacement unit decreases when said displacement unit is transferred from said delivery state to said activated state.

6. The medical system according to claim 1, wherein said proximal expandable portion has a larger expanded diameter than said distal anchoring portion in said activated state of the displacement unit.

7. The medical system according to claim 1, wherein said distal anchoring portion is expandable to anchor against said coronary sinus in said activated state of the displacement unit.

8. The medical system according to claim 1, wherein said distal anchoring portion comprises an expandable coiled wire.

9. The medical system according to claim 8, wherein said coiled wire is connected to a control wire that is adapted to stretch said distal anchoring portion to a reduced diameter delivery shape, and reduce tension on said coiled wire in said activated state to expand said distal anchoring portion.

10. The medical system according to claim 1, wherein when said proximal expandable portion is expanded to the delivery state, said proximal expandable portion has a diameter substantially larger than a diameter of said coronary sinus.

11. The medical system according to claim 1, wherein said fixation structure comprises a helix-shaped loop structure for positioning on either side of said valve to retain said modified shape of the annulus, wherein at least a portion of the helix-shaped loop structure conforms to a curvature of said annulus.

12. The medical system according to claim 11, wherein at least a portion of the displacement unit is movable to an activated shape that at least partly assumes the curvature of said loop structure.

13. The medical system according to claim 1, wherein said annuloplasty device is catheter deliverable.

14. The medical system according to claim 1, wherein said distal anchoring portion comprises a tissue retention portion.

15. The medical system according to claim 14, wherein said tissue retention portion is expandable in a direction substantially perpendicular to said longitudinal direction, and/or
wherein a tissue apposition portion is expandable in a direction substantially perpendicular to said longitudinal direction.

16. The medical system according to claim 15, wherein said tissue retention portion and said tissue apposition portion are expandable in substantially opposite directions.

17. The medical system according to claim 1, wherein said anchoring portion comprises a tissue apposition portion having a tissue atraumatic surface, such as an at least partly curved or spherical surface.

18. The medical system according to claim 1, wherein said displacement unit comprises, at a radial portion thereof, at least one radiopaque marker for rotational alignment of said displacement unit in said coronary sinus.

19. A removable and flexible elongate displacement unit for temporary insertion into a coronary sinus adjacent a defective mitral valve having an annulus, wherein said displacement unit has
a delivery state for delivery into said coronary sinus, and
an activated state to which the displacement unit is temporarily and reversibly transferable from said delivery state, said displacement unit comprises
a proximal reversibly expandable portion,
a distal anchoring portion being movable in relation to said proximal expandable portion in a longitudinal direction of said displacement unit to said activated state in which the shape of the annulus is modified to a modified shape wherein the proximal expandable portion comprises first and second expandable loops, wherein in the delivery state said proximal expandable portion is compressed within a sheath, and the first and second loops are folded such as to be parallel with the longitudinal axis, and wherein in the activated state said proximal expandable portion is expanded, out of the sheath, wherein the first and second loops pivot away from a longitudinal axis, of the displacement unit, in opposite directions from one another for positioning against a tissue wall outside the entrance of said coronary sinus for providing a counter force against said distal anchoring portion.

* * * * *